United States Patent [19]
Fischer et al.

[11] Patent Number: 5,977,029
[45] Date of Patent: Nov. 2, 1999

[54] 3-ARYL-5-HALOGEN-PYRONE DERIVATIVES AS PEST CONTROL AGENTS

[75] Inventors: Reiner Fischer, Monheim; Folker Lieb, Leverkusen; Michael Ruther, Monheim; Jörg Stetter, Wuppertal; Markus Dollinger, Leverkusen; Christoph Erdelen, Leichlingen; Norbert Mencke; Hans-Joachim Santel, both of Leverkusen; Andreas Turberg, Erkrath; Ulrike Wachendorff-Neumann, Neuwied, all of Germany

[73] Assignee: Bayer Aktiengesellschaft, Leverkusen, Germany

[21] Appl. No.: 09/051,881
[22] PCT Filed: Oct. 15, 1996
[86] PCT No.: PCT/EP96/04475
  § 371 Date: Apr. 20, 1998
  § 102(e) Date: Apr. 20, 1998
[87] PCT Pub. No.: WO97/16436
  PCT Pub. Date: May 9, 1997

[30] Foreign Application Priority Data

Oct. 27, 1995 [DE] Germany .............. 195 40 080

[51] Int. Cl.⁶ .............. A01N 43/14; C07D 309/30
[52] U.S. Cl. .............. 504/292; 549/291; 549/293; 549/292; 549/416
[58] Field of Search .............. 549/291, 292, 549/293, 416; 504/292

[56] References Cited

U.S. PATENT DOCUMENTS 5,393,729  2/1995  Fischer et al. .............. 504/128

FOREIGN PATENT DOCUMENTS 0 588 137  3/1994  European Pat. Off. .

*Primary Examiner*—Amelia Owens
*Attorney, Agent, or Firm*—Sprung Kramer Schaefer & Briscoe

[57] ABSTRACT

The invention relates to novel 3-aryl-5-halogeno-pyrone derivatives of the formula (I)

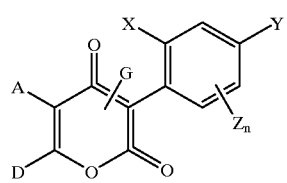

in which

A, D, G, X, Y, Z and n are each as defined in the description, to a plurality of processes and intermediates for their preparation and to their use as pesticides and herbicides.

7 Claims, No Drawings

3-ARYL-5-HALOGEN-PYRONE DERIVATIVES AS PEST CONTROL AGENTS

This application is a 371 of PCT/E96/04475 filed Oct. 15, 1996.

The invention relates to novel 3-aryl-5-halogeno-pyrone derivatives, to a plurality of processes and intermediates for their preparation and to their use as pesticides and herbicides.

Certain phenyl-pyrone derivatives without substitution in the phenyl ring have already been disclosed (cf. A. M. Chirazi, T. Kappe and E. Ziegler, Arch. Pharm. 309, 558 (1976) and K.-H. Boltze and K. Heidenbluth, Chem. Ber. 91, 2849 (1958)), but a possible use as pesticides has not been mentioned for these compounds. Phenyl-pyrone derivatives with substitution in the phenyl ring having herbicidal, acaricidal and insecticidal properties are described in EP-A-588 137.

However, the efficacy and the spectrum of activity of these compounds is, in particular at low application rates and concentrations, not always entirely satisfactory. Moreover, the crop safety is frequently insufficient.

This invention, accordingly, provides novel compounds of the formula (I)

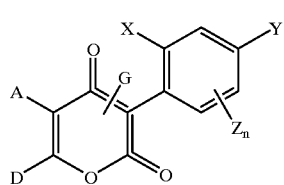

(I)

in which

- X represents halogen, nitro, cyano, alkyl, alkenyl, alkoxy, alkenyloxy, alkylthio, alkylsulphinyl, alkylsulphonyl, halogenoalkyl, halogenoalkenyl, halogenoalkoxy, halogenoalkenyloxy or respectively optionally substituted phenyl, phenoxy, phenylthio, benzyloxy or benzylthio,
- Y represents hydrogen, halogen, nitro, cyano, alkyl, alkenyl, alkoxy, alkenyloxy, alkylthio, alkylsulphinyl, alkylsulphonyl, halogenoalkyl, halogenoalkenyl, halogenoalkoxy or halogenoalkenyloxy,
- Z represents halogen, nitro, cyano, alkyl, alkenyl, alkoxy, alkenyloxy, halogenoalkyl, halogenoalkenyl, halogenoalkoxy or halogenoalkenyloxy,
- n represents one of the numbers 0, 1, 2 or 3,
- A represents halogen,
- D represents hydrogen or represents an optionally substituted radical from the group consisting of alkyl, alkenyl, alkinyl, alkoxyalkyl, polyalkoxyalkyl, alkylthioalkyl, saturated or unsaturated cycloalkyl, saturated or unsaturated heterocyclyl, arylalkyl, aryl, hetarylalkyl and hetaryl and
- G represents hydrogen (a) or represents one of the groups (b)

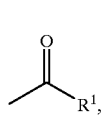

(c)

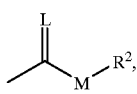

(d)

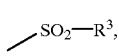

(e)

(f)

E or (g)

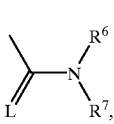

in which

- E represents a metal ion equivalent or an ammonium ion,
- L represents oxygen or sulphur,
- M represents oxygen or sulphur,
- $R^1$ represents respectively optionally halogen-substituted alkyl, alkenyl, alkoxyalkyl alkylthioalkyl or polyalkoxyalkyl or represents respectively optionally halogen-, alkyl- or alkoxy-substituted cycloalkyl or heterocyclyl or represents respectively optionally substituted phenyl, phenylalkyl, hetaryl, phenoxyalkyl or hetaryloxyalkyl,
- $R^2$ represents respectively optionally halogen-substituted alkyl, alkenyl, alkoxyalkyl or polyalkoxyalkyl or represents respectively optionally substituted cycloalkyl, phenyl or benzyl,
- $R^3$, $R^4$ and $R^5$ independently of one another each represent respectively optionally halogen-substituted alkyl, alkoxy, alkylamino, dialkylamino, alkylthio, alkenylthio or cycloalkylthio or represent respectively optionally substituted phenyl, benzyl, phenoxy or phenylthio,
- $R^6$ and $R^7$ independently of one another each represent hydrogen, represent respectively optionally halogen-substituted alkyl, cycloalkyl, alkenyl, alkoxy, alkoxyalkyl, represent respectively optionally substituted phenyl or benzyl, or, together with the linking nitrogen atom, form an optionally oxygen- or sulphur-containing cycle.

Depending inter alia on the nature of the substituents, the compounds of the formula (I) may be present as geometric and/or optical isomers or mixtures of isomers, in varying composition, which can, if appropriate, be separated in a customary manner. The present invention provides both the pure isomers and the isomer mixtures, their preparation and their use and compositions comprising them. Hereinbelow, for the sake of simplicity, reference is always made to compounds of the formula (I) although this includes both the pure compounds and, if appropriate, also mixtures having varying proportions of isomeric compounds.

Depending on the position of the substituent G, the compounds of the formula (I) may be present in the two isomeric forms of formulae $(I)_a$ and $(I)_b$

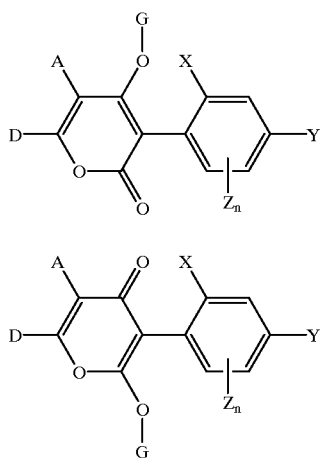

(I)a (I)b which is meant to be expressed by the dotted line in the formula (I).

The compounds of the formulae (I)$_a$ and (I)$_b$ may be present both as mixtures and in the form of their pure isomers. If appropriate, mixtures of the compounds of the formulae (I)$_a$ and (I)$_b$ may be separated by physical methods in a manner known per se, for example by chromatographic methods.

For the sake of clarity, hereinbelow only one of the possible isomers is given in each case. It is implied that the compounds may be present in the form of isomer mixtures or in the other isomeric form in question.

Including the various meanings (a), (b), (c), (d), (e), (f) and (g) of group G, the following main structures (I-a) to (I-g) result

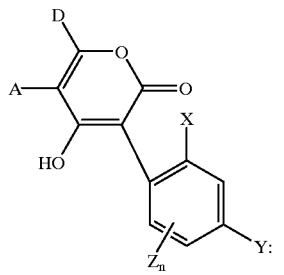

(I-a)

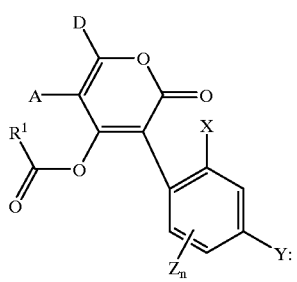

(I-b)

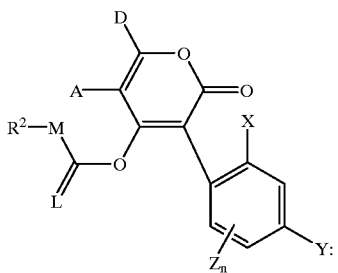

(I-c)

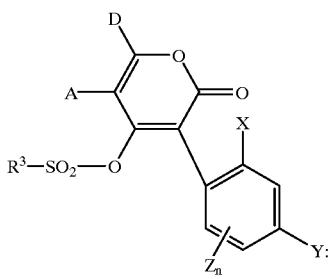

(I-d)

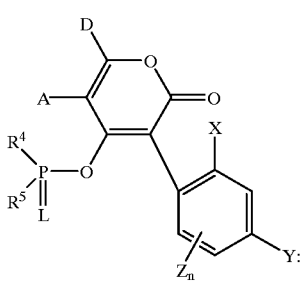

(I-e)

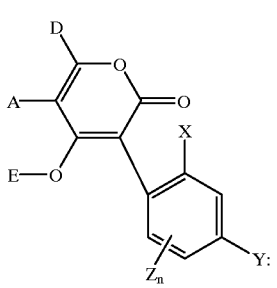

(I-f)

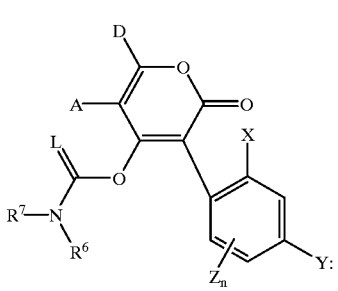

(I-g)

in which

A, D, E, L, M, X, Y, Z, $R^1$, $R^2$, $R^3$, $R^4$, $R^5$, $R^6$, $R^7$ and n are each as defined above.

Furthermore, it has been found that the novel compounds of the formula (I) are obtained by one of the processes described below.

(A) The compounds of the formula (I-a)

(I-a)

in which
A, D, X, Y, Z and n are each as defined above
are obtained when
Compounds of the formula (II)

(II)

$$D-\overset{O}{\underset{\|}{C}}-CH_2-A$$

in which
A and D are each as defined above
are reacted with compounds of the formula (III)

(III)

in which
X, Y, Z and n are each as defined above and
Hal represents halogen (preferably chlorine or bromine),
if appropriate in the presence of a diluent and if appropriate in the presence of an acid acceptor.

(B) Compounds of the formula (I-b) shown above in which A, D, $R^1$, X, Y, Z and n are each as defined above are obtained when compounds of the formula (I-a) shown above in which A, D, X, Y, Z and n are each as defined above are reacted α) with acyl halides of the formula (IV)

(IV)

in which
$R^1$ is as defined above and
Hal represents halogen (in particular chlorine or bromine) or β) with carboxylic anhydrides of the formula (V)

$$R^1-CO-O-CO-R^1 \qquad (V)$$

in which
$R^1$ is as defined above,
if appropriate in the presence of a diluent and if appropriate in the presence of an acid binder.

(C) Compounds of the formula (I-c) shown above in which A, D, $R^2$, M, X, Y, Z and n are each as defined above and L represents oxygen are obtained when compounds of the formula (I-a) shown above in which A, D, X, Y, Z and n are each as defined above are reacted with chloroformic acid esters or chloroformic acid thioesters of the formula (VI)

$$R^2-M-CO-Cl \qquad (VI)$$

in which
$R^2$ and M are each as defined above,
if appropriate in the presence of a diluent and if appropriate in the presence of an acid binder.

(D) Compounds of the formula (I-c) shown above in which A, D, $R^2$, M, X, Y, Z and n are each as defined above and L represents sulphur are obtained when compounds of the formula (I-a) shown above in which A, D, X, Y, Z and n are each as defined above are reacted α) with chloromonothioformic acid esters or chlorodithioformic acid esters of the formula (VII)

(VII)

in which
M and $R^2$ are each as defined above,
if appropriate in the presence of a diluent and if appropriate in the presence of an acid binder or β) with carbon disulphide and subsequently with compounds of the formula (VIII)

$$R^2-Hal \qquad (VIII)$$

in which
$R^2$ is as defined above and
Hal represents chlorine, bromine or iodine,
if appropriate in the presence of a diluent and if appropriate in the presence of a base.

(E) Compounds of the formula (I-d) shown above in which A, D, $R^3$, X, Y, Z and n are each as defined above are obtained when compounds of the formula (I-a) shown above in which A, D, X, Y, Z and n are each as defined above are in each case reacted with sulphonyl chlorides of the formula (IX)

$$R^3-SO_2-Cl \qquad (IX)$$

in which
$R^3$ is as defined above,
if appropriate in the presence of a diluent and if appropriate in the presence of an acid binder.

(F) Compounds of the formula (I-e) shown above in which A, D, L, $R^4$, $R^5$, X, Y, Z and n are each as defined above are obtained when compounds of the formula (I-a) shown above in which A, D, X, Y, Z and n are each as defined above are in each case reacted with phosphorus compounds of the formula (X)

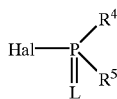
(X)

in which
L, $R^4$ and $R^5$ are each as defined above and
Hal represents halogen (in particular chlorine or bromine),
if appropriate in the presence of a diluent and if appropriate in the presence of an acid binder.

(G) Compounds of the formula (I-f) shown above in which A, D, E, X, Y, Z and n are each as defined above are obtained when compounds of the formula (I-a) in which A, D, X, Y, Z and n are each as defined above are in each case reacted
with metal compounds or amines of the formulae (XI) or (XII)

(XI)

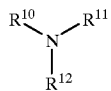
(XII)

in which
Me represents a mono- or bivalent metal (preferably an alkali metal or an alkaline earth metal such as lithium, sodium, potassium, magnesium or calcium), t represents the number 1 or 2 and
$R^9$, $R^{10}$, $R^{11}$, $R^{12}$ independently of one another each represent hydrogen or alkyl (preferably $C_1$–$C_8$-alkyl),
if appropriate in the presence of a diluent.

(H) Compounds of the formula (I-g) shown above in which A, D, L, $R^6$, $R^7$, X, Y, Z and n are each as defined above are obtained when compounds of the formula (I-a) shown above in which A, D, X, Y, Z and n are each as defined above are in each case reacted α) with isocyanates or isothiocyanates of the formula (XIII)

(XIII)

in which
$R^6$ and L are each as defined above,
if appropriate in the presence of a diluent and if appropriate in the presence of a catalyst or β) with carbamyl chlorides or thiocarbamyl chlorides of the formula (XIV)

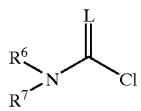
(XIV)

in which
L, $R^6$ and $R^7$ are each as defined above,
if appropriate in the presence of a diluent and if appropriate in the presence of an acid binder.

Furthermore, it has been found that the novel compounds of the formula (I) have very high activity as pesticides, preferably as insecticides and acaricides, while having good plant safety. Herbicidal activity has been observed preferably at relatively high application rates.

The formula (I) provides a general definition of the compounds according to the invention. Preferred substituents and ranges of the radicals listed in the formulae mentioned hereinabove and hereinbelow are illustrated below:

X preferably represents fluorine, chlorine, bromine, iodine, nitro, cyano, $C_1$–$C_8$-alkyl, $C_2$–$C_6$-alkenyl, $C_1$–$C_6$-alkoxy, $C_2$–$C_6$-alkenyloxy, $C_1$–$C_6$-alkylthio, $C_1$–$C_6$-alkylsulphinyl, $C_1$–$C_6$-alkylsulphonyl, represents respectively fluorine-, chlorine- or bromine-substituted $C_1$–$C_6$-alkyl, $C_2$–$C_6$-alkenyl, $C_1$–$C_6$-alkoxy or $C_2$–$C_6$-alkenyloxy or represents phenyl, phenoxy, phenylthio, benzyloxy or benzylthio, each of which is optionally substituted by fluorine, chlorine, bromine, iodine, nitro, cyano, or by respectively optionally fluorine-, chlorine- or bromine-substituted $C_1$–$C_6$-alkyl or $C_1$–$C_6$-alkoxy.

Y preferably represents hydrogen, fluorine, chlorine, bromine, iodine, nitro, cyano, $C_1$–$C_8$-alkyl, $C_2$–$C_6$-alkenyl, $C_1$–$C_6$-alkoxy, $C_2$–$C_6$-alkenyloxy, $C_1$–$C_6$-alkylthio, $C_1$–$C_6$-alkylsulphinyl, $C_1$–$C_6$-alkylsulphonyl or represents respectively fluorine-, chlorine- or bromine-substituted $C_1$–$C_6$-alkyl, $C_2$–$C_6$-alkenyl, $C_1$–$C_6$-alkoxy or $C_2$–$C_6$-alkenyloxy.

Z preferably represents fluorine, chlorine, bromine, iodine, nitro, cyano, $C_1$–$C_8$-alkyl, $C_2$–$C_6$-alkenyl, $C_1$–$C_6$-alkoxy, $C_2$–$C_6$-alkenyloxy or respectively fluorine-, chlorine- or bromine-substituted $C_1$–$C_6$-alkyl, $C_2$–$C_6$-alkenyl, $C_1$–$C_6$-alkoxy or $C_2$–$C_6$-alkenyloxy.

n preferably represents one of the numbers 0, 1, 2 or 3.

A preferably represents fluorine, chlorine, bromine or iodine.

D preferably represents hydrogen, represents respectively optionally halogen-substituted $C_1$–$C_{12}$-alkyl, $C_3$–$C_8$-alkenyl, $C_3$–$C_8$-alkinyl, $C_1$–$C_{10}$-alkoxy-$C_2$–$C_8$-alkyl, poly-$C_1$–$C_8$-alkoxy-$C_2$–$C_8$-alkyl or $C_1$–$C_{10}$-alkylthio-$C_2$–$C_8$-alkyl, represents cyano-, $C_1$–$C_8$-alkyloxycarbonyl- or $C_1$–$C_8$-alkylcarbonyloxy-substituted $C_1$–$C_{12}$-alkyl, represents optionally halogen-, $C_1$–$C_4$-alkyl, $C_1$–$C_4$-alkoxy- or $C_1$–$C_4$-halogenoalkyl-substituted $C_3$–$C_8$-cycloalkyl in which optionally one or two not directly adjacent methylene groups are replaced by oxygen and/or sulphur or represents respectively optionally halogen-, $C_1$–$C_6$-alkyl-, $C_1$–$C_6$-halogenoalkyl-, $C_1$–$C_6$-alkoxy-, $C_1$–$C_6$-halogenoalkoxy-, cyano- or nitro-substituted phenyl, hetaryl having 5 to 6 ring atoms and one or two hetero atoms from the group consisting of oxygen, sulphur and nitrogen, phenyl-$C_1$–$C_6$-alkyl or hetaryl-$C_1$–$C_6$-alkyl having 5 to 6 ring atoms and one or two hetero atoms from the group consisting of oxygen, sulphur and nitrogen.

G preferably represents hydrogen (a) or represents one of the groups

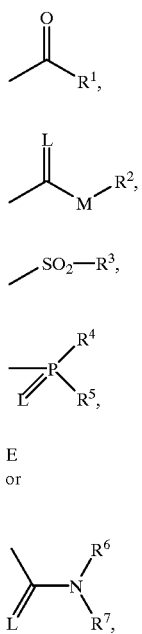

(b), (c), (d), (e), (f), (g)

in which

E represents a metal ion equivalent or an ammonium ion,

L represents oxygen or sulphur and

M represents oxygen or sulphur.

$R^1$ preferably represents respectively optionally halogen-substituted $C_1-C_{20}$-alkyl, $C_2-C_{20}$-alkenyl, $C_1-C_8$-alkoxy-$C_1-C_8$-alkyl, $C_1-C_8$-alkylthio-$C_1-C_8$-alkyl or poly-$C_1-C_8$-alkoxy-$C_1-C_8$-alkyl or represents optionally halogen-, $C_1-C_6$-alkyl- or $C_1-C_6$-alkoxy-substituted $C_3-C_8$-cycloalkyl in which optionally one or two not directly adjacent methylene groups are replaced by oxygen and/or sulphur, represents optionally halogen-, cyano-, nitro-, $C_1-C_6$-alkyl-, $C_1-C_6$-alkoxy-, $C_1-C_6$-halogenoalkyl-, $C_1-C_6$-halogenoalkoxy-, $C_1-C_6$-alkylthio- or $C_1-C_6$-alkylsulphonyl-substituted phenyl, represents optionally halogen-, nitro-, cyano-, $C_1-C_6$-alkyl-, $C_1-C_6$-alkoxy-, $C_1-C_6$-halogenoalkyl- or $C_1-C_6$-halogenoalkoxy-substituted phenyl-$C_1-C_6$-alkyl, represents optionally halogen- or $C_1-C_6$-alkyl-substituted 5- or 6-membered hetaryl having one or two hetero atoms from the group consisting of oxygen, sulphur and nitrogen, represents optionally halogen- or $C_1-C_6$-alkyl-substituted phenoxy-$C_1-C_6$-alkyl or represents optionally halogen-, amino- or $C_1-C_6$-alkyl-substituted 5- or 6-membered hetaryloxy-$C_1-C_6$-alkyl having one or two hetero atoms from the group consisting of oxygen, sulphur and nitrogen.

$R^2$ preferably represents respectively optionally halogen-substituted $C_1-C_{20}$-alkyl, $C_2-C_{20}$-alkenyl, $C_1-C_8$-alkoxy-$C_2-C_8$-alkyl- or poly-$C_1-C_8$-alkoxy-$C_2-C_8$-alkyl, represents optionally halogen-, $C_1-C_6$-alkyl- or $C_1-C_6$-alkoxy-substituted $C_3-C_8$-cycloalkyl or represents respectively optionally halogen-, cyano-, nitro-, $C_1-C_6$-alkyl-, $C_1-C_6$-alkoxy-, $C_1-C_6$-halogenoalkyl- or $C_1-C_6$-halogenoalkoxy-substituted phenyl or benzyl.

$R^3$ preferably represents optionally halogen-substituted $C_1-C_8$-alkyl or represents respectively optionally halogen-, $C_1-C_6$-alkyl-, $C_1-C_6$-alkoxy-, $C_1-C_4$-halogenoalkyl-, $C_1-C_4$-halogenoalkoxy-, cyano- or nitro-substituted phenyl or benzyl.

$R^4$ and $R^5$ independently of one another each preferably represent respectively optionally halogen-substituted $C_1-C_8$-alkyl, $C_1-C_8$-alkoxy, $C_1-C_8$-alkylamino, di-($C_1-C_8$-alkyl)amino, $C_1-C_8$-alkylthio or $C_2-C_8$-alkenylthio or represent respectively optionally halogen-, nitro-, cyano-, $C_1-C_4$-alkoxy-, $C_1-C_4$-halogenoalkoxy-, $C_1-C_4$-alkylthio-, $C_1-C_4$-halogenoalkylthio-, $C_1-C_4$-alkyl- or $C_1-C_4$-halogenoalkyl-substituted phenyl, phenoxy or phenylthio.

$R^6$ and $R^7$ independently of one another each preferably represent hydrogen, represent respectively optionally halogen-substituted $C_1-C_8$-alkyl, $C_3-C_8$-cycloalkyl, $C_1-C_8$-alkoxy, $C_3-C_8$-alkenyl or $C_1-C_8$-alkoxy-$C_2-C_8$-alkyl, represent respectively optionally halogen-, $C_1-C_8$-alkyl-, $C_1-C_8$-halogenoalkyl- or $C_1-C_8$-alkoxy-substituted phenyl or benzyl or together represent a $C_3-C_6$-alkylene radical in which optionally one methylene group is replaced by oxygen or sulphur.

X particularly preferably represents fluorine, chlorine, bromine, nitro, cyano, $C_1-C_6$-alkyl, $C_2-C_4$-alkenyl, $C_1-C_4$-alkoxy, $C_2-C_4$-alkenyloxy, $C_1-C_4$-alkylthio, $C_1-C_4$-alkylsulphinyl, $C_1-C_4$-alkylsulphonyl, represents respectively fluorine- or chlorine-substituted $C_1-C_4$-alkyl, $C_2-C_4$-alkenyl, $C_1-C_4$-alkoxy or $C_2-C_4$-alkenyloxy or represents phenyl, phenoxy, phenylthio, benzyloxy or benzylthio, each of which is optionally substituted by fluorine, chlorine, bromine, nitro, cyano or by respectively optionally fluorine- or chlorine-substituted $C_1-C_4$-alkyl or $C_1-C_4$-alkoxy.

Y particularly preferably represents hydrogen, fluorine, chlorine, bromine, nitro, cyano, $C_1-C_6$-alkyl, $C_2-C_4$-alkenyl, $C_1-C_4$-alkoxy, $C_2-C_4$-alkenyloxy, $C_1-C_4$-alkylthio, $C_1-C_4$-alkylsulphinyl, $C_1-C_4$-alkylsulphonyl or represents respectively fluorine- or chlorine-substituted $C_1-C_4$-alkyl or $C_1-C_4$-alkoxy.

Z particularly preferably represents fluorine, chlorine, bromine, nitro, cyano, $C_1-C_6$-alkyl, $C_1-C_4$-alkoxy, $C_2-C_4$-alkenyloxy or respectively fluorine- or chlorine-substituted $C_1-C_4$-alkyl or $C_1-C_4$-alkoxy.

n particularly preferably represents one of the numbers 0, 1 or 2.

A particularly preferably represents fluorine, chlorine or bromine.

D particularly preferably represents hydrogen, represents respectively optionally fluorine- or chlorine-substituted $C_1-C_{10}$-alkyl, $C_3-C_6$-alkenyl, $C_3-C_6$-alkinyl, $C_1-C_8$-alkoxy-$C_2-C_6$-alkyl, poly-$C_1-C_6$-alkoxy-$C_2-C_6$-alkyl or $C_1-C_8$-alkylthio-$C_214 C_6$-alkyl, represents cyano-, $C_1-C_6$-alkoxycarbonyl- or $C_1-C_6$-alkylcarbonyloxy-substituted $C_1-C_8$-alkyl, represents optionally fluorine-, chlorine-, $C_1-C_4$-alkyl-, $C_1-C_4$-alkoxy- or $C_1-C_2$-halogenoalkyl-substituted $C_3-C_7$-cycloalkyl in which optionally one or two not directly adjacent methylene groups are replaced by oxygen and/or sulphur or represents respectively optionally fluorine-, chlorine-, bromine-, $C_1$–$C_4$-alkyl-, $C_1$–$C_4$-halogenoalkyl-, $C_1$–$C_4$-alkoxy-, $C_1$–$C_4$-halogenoalkoxy-, cyano- or nitro-substituted phenyl, furanyl, imidazolyl, pyridyl, thiazolyl, pyrazolyl, pyrimidyl, pyridazyl, pyrazinyl, pyrrolyl, thienyl, triazolyl or phenyl-$C_1$–$C_4$-alkyl.

G particularly preferably represents hydrogen (a) or represents one of the groups

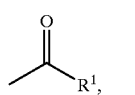
(b)

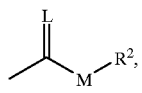
(c)

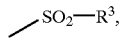
(d)

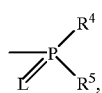
(e)

(f)
E or

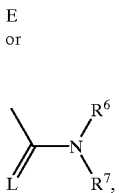
(g)

in which
E represents a metal ion equivalent or an ammonium ion,
L represents oxygen or sulphur and
M represents oxygen or sulphur.

$R^1$ particularly preferably represents respectively optionally fluorine- or chlorine-substituted $C_1$–$C_{16}$-alkyl, $C_2$–$C_{16}$-alkenyl, $C_1$–$C_6$-alkoxy-$C_1$–$C_6$-alkyl, $C_1$–$C_6$-alkylthio-$C_1$–$C_6$-alkyl or poly-$C_1$–$C_6$-alkoxy-$C_1$–$C_6$-alkyl or represents optionally fluorine-, chlorine-, $C_1$–$C_5$-alkyl- or $C_1$–$C_5$-alkoxy-substituted $C_3$–$C_7$-cycloalkyl in which optionally one or two not directly adjacent methylene groups are replaced by oxygen and/or sulphur, represents optionally fluorine-, chlorine-, bromine-, cyano-, nitro-, $C_1$–$C_4$-alkyl-, $C_1$–$C_4$-alkoxy-, $C_1$–$C_3$-halogenoalkyl-, $C_1$–$C_3$-halogenoalkoxy-, $C_1$–$C_4$-alkylthio- or $C_1$–$C_4$-alkylsulphonyl-substituted phenyl, represents optionally fluorine-, chlorine-, bromine-, $C_1$–$C_4$-alkyl-, $C_1$–$C_4$-alkoxy-, $C_1$–$C_3$-halogenoalkyl- or $C_1$–$C_3$-halogenoalkoxy-substituted phenyl-$C_1$–$C_4$-alkyl, represents respectively optionally fluorine-, chlorine-, bromine- or $C_1$–$C_4$-alkyl-substituted pyrazolyl, thiazolyl, pyridyl, pyrimidyl, furanyl or thienyl, represents optionally fluorine-, chlorine-, bromine- or $C_1$–$C_4$-alkyl-substituted phenoxy-$C_1$–$C_5$-alkyl or represents respectively optionally fluorine-, chlorine-, bromine-, amino- or $C_1$–$C_4$-alkyl-substituted pyridyloxy-$C_1$–$C_5$-alkyl, pyrimidyloxy-$C_1$–$C_5$-alkyl or thiazolyloxy-$C_1$–$C_5$-alkyl.

$R^2$ particularly preferably represents respectively optionally fluorine- or chlorine-substituted $C_1$–$C_{16}$-alkyl, $C_2$–$C_{16}$-alkenyl, $C_1$–$C_6$-alkoxy-$C_2$–$C_6$-alkyl or poly-$C_1$–$C_6$-alkoxy-$C_2$–$C_6$-alkyl, represents optionally fluorine-, chlorine-, $CC_1$–$C_4$-alkyl- or $C_1$–$C_4$-alkoxy-substituted $C_3$–$C_7$-cycloalkyl or represents respectively optionally fluorine-, chlorine-, bromine-, cyano-, nitro-, $C_1$–$C_4$-alkyl-, $C_1$–$C_3$-alkoxy, $C_1$–$C_3$-halogenoalkyl or $C_1$–$C_3$-halogenoalkoxy-substituted phenyl or benzyl.

$R^3$ particularly preferably represents optionally fluorine- or chlorine-substituted $C_1$–$C_6$-alkyl or represents respectively optionally fluorine-, chlorine-, bromine-, $C_1$–$C_5$-alkyl-, $C_1$–$C_5$-alkoxy-, $C_1$–$C_3$-halogenoalkyl-, $C_1$–$C_3$-halogenoalkoxy-, cyano- or nitro-substituted phenyl or benzyl.

$R^4$ and $R^5$ independently of one another each particularly preferably represent respectively optionally fluorine- or chlorine-substituted $C_1$–$C_6$-alkyl, $C_1$–$C_6$-alkoxy, $C_1$–$C_6$-alkylamino, di-($C_1$–$C_6$-alkyl) amino, $C_1$–$C_6$-alkylthio or $C_3$–$C_4$-alkenylthio or represent respectively optionally fluorine-, chlorine-, bromine-, nitro-, cyano-, $C_1$–$C_3$-alkoxy-, $C_1$–$C_3$-halogenoalkoxy-, $C_1$–$C_3$-alkylthio-, $C_1$–$C_3$-halogenoalkylthio-, $C_1$–$C_3$-alkyl- or $C_1$–$C_3$-halogenoalkyl-substituted phenyl, phenoxy or phenylthio.

$R^6$ and $R^7$ independently of one another each particularly preferably represent hydrogen, represent respectively optionally fluorine- or chlorine-substituted $C_1$–$C_6$-alkyl, $C_3$–$C_6$-cycloalkyl, $C_1$–$C_6$-alkoxy, $C_3$–$C_6$-alkenyl or $C_1$–$C_6$-alkoxy-$C_2$–$C_6$-alkyl, represent respectively optionally fluorine-, chlorine-, bromine-, $C_1$–$C_5$-halogenoalkyl-, $C_1$–$C_5$-alkyl- or $C_1$–$C_5$-alkoxy-substituted phenyl or benzyl, or together represent a $C_3$–$C_6$-alkylene radical in which optionally one methylene group is replaced by oxygen or sulphur.

X very particularly preferably represents fluorine, chlorine, bromine, nitro, cyano, methyl, ethyl, n- or i-propyl, n-, s-, i- or t-butyl, vinyl, allyl, methallyl, methoxy, ethoxy, n- or i-propoxy, allyloxy, methallyloxy, trifluoromethyl, difluoromethoxy, trifluoromethoxy, trifluoroethoxy, methylthio, methylsulphinyl or methylsulphonyl.

Y very particularly preferably represents hydrogen, fluorine, chlorine, bromine, nitro, cyano, methyl, ethyl, n- or i-propyl, n-, s-, i- or t-butyl, methoxy, ethoxy, n- or i-propoxy, allyloxy, methallyloxy, trifluoromethyl, difluoromethoxy, trifluoromethoxy, trifluoroethoxy, methylthio, methylsulphinyl or methylsulphonyl.

Z very particularly preferably represents fluorine, chlorine, bromine, nitro, cyano, methyl, ethyl, n- or i-propyl, n-, s-, i- or t-butyl, methoxy, ethoxy, n- or i-propoxy, allyloxy, methallyloxy, trifluoromethyl, difluoromethoxy, trifluoromethoxy or trifluoroethoxy.

n very particularly preferably represents one of the numbers 0 or 1.

A very particularly preferably represents fluorine, chlorine or bromine.

D very particularly preferably represents hydrogen, represents respectively optionally fluorine- or chlorine-substituted $C_1$–$C_8$-alkyl, $C_3$–$C_4$-alkenyl, $C_3$–$C_4$- alkinyl, $C_1$–$C_6$-alkoxy-$C_2$–$C_4$-alkyl, poly-$C_1$–$C_4$-alkoxy-$C_2$–$C_4$-alkyl, $C_1$–$C_4$-alkylthio-$C_2$–$C_4$-alkyl or $C_3$–$C_6$-cycloalkyl in which optionally one or two not directly adjacent methylene groups are replaced by oxygen and/or sulphur or represents respectively optionally fluorine-, chlorine-, bromine-, methyl-, ethyl-, n-propyl-, isopropyl-, methoxy-, ethoxy-, trifluoromethyl-, trifluoromethoxy-, cyano- or nitro-substituted phenyl, furanyl, pyridyl, thienyl or benzyl.

G very particularly preferably represents hydrogen (a) or represents one of the groups

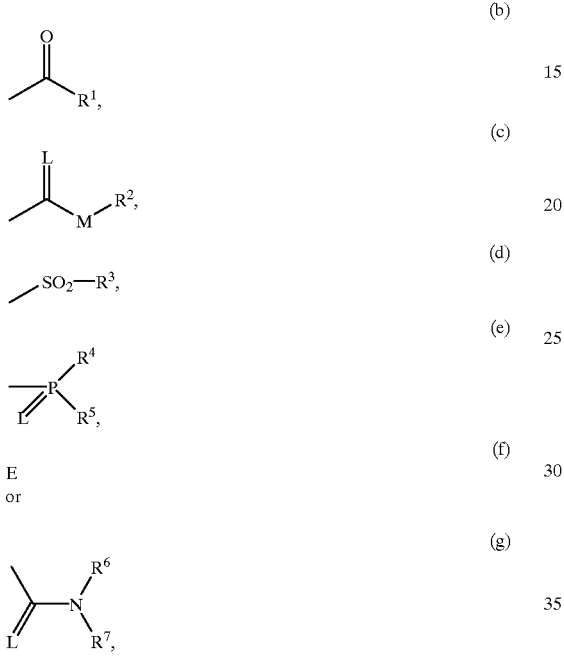

in which

E represents a metal ion equivalent or an ammonium ion,

L represents oxygen or sulphur and

M represents oxygen or sulphur.

$R^1$ very particularly preferably represents respectively optionally fluorine- or chlorine-substituted $C_1$–$C_{14}$-alkyl, $C_2$–$C_{14}$-alkenyl, $C_1$–$C_4$-alkoxy-$C_1$–$C_6$-alkyl, $C_1$–$C_4$-alkylthio-$C_1$–$C_6$-alkyl, poly-$C_1$–$C_4$-alkoxy-$C_1$–$C_4$-alkyl or represents optionally fluorine-, chlorine-, methyl-, ethyl-, n-propyl-, i-propyl-, n-butyl, i-butyl-, tert-butyl-, methoxy-, ethoxy-, n-propoxy- or isopropoxy-substituted $C_3$–$C_6$-cycloalkyl in which optionally one or two not directly adjacent methylene groups are replaced by oxygen and/or sulphur, represents optionally fluorine-, chlorine-, bromine-, cyano-, nitro-, methyl-, ethyl-, n-propyl-, i-propyl-, methoxy-, ethoxy-, trifluoromethyl-, trifluoromethoxy-, methylthio-, ethylthio-, methylsulphonyl- or ethylsulphonyl-substituted phenyl, represents optionally fluorine-, chlorine-, bromine-, methyl-, ethyl-, n-propyl-, i-propyl-, methoxy-, ethoxy-, trifluoromethyl- or trifluoromethoxy-substituted benzyl, represents respectively optionally fluorine-, chlorine-, bromine-, methyl- or ethyl-substituted furanyl, thienyl or pyridyl, represents optionally fluorine-, chlorine-, methyl- or ethyl-substituted phenoxy-$C_1$–$C_4$-alkyl or represents respectively optionally fluorine-, chlorine-, amino-, methyl- or ethyl-substituted pyridyloxy-$C_1$–$C_4$-alkyl, pyrimidyloxy-$C_1$–$C_4$-alkyl or thiazolyloxy-$C_1$–$C_4$-alkyl.

$R^2$ very particularly preferably represents respectively optionally fluorine- or chlorine-substituted $C_1$–$C_{14}$-alkyl, $C_2$–$C_{14}$-alkenyl, $C_1$–$C_4$-alkoxy-$C_2$–$C_6$-alkyl or poly-$C_1$–$C_4$-alkoxy-$C_2$–$C_6$-alkyl, represents optionally fluorine-, chlorine-, methyl-, ethyl-, n-propyl-, isopropyl- or methoxy-substituted $C_3$–$C_6$-cycloalkyl, or represents respectively optionally fluorine-, chlorine-, cyano-, nitro-, methyl-, ethyl-, n-propyl-, i-propyl-, methoxy-, ethoxy-, trifluoromethyl- or trifluoromethoxy-substituted phenyl or benzyl.

$R^3$ very particularly preferably represents optionally fluorine- or chlorine-substituted methyl, ethyl, propyl, isopropyl or respectively optionally fluorine-, chlorine-, bromine-, methyl-, ethyl-, propyl-, isopropyl-, tert-butyl-, methoxy-, ethoxy-, isopropoxy-, tert-butoxy-, trifluoromethyl-, trifluoromethoxy-, cyano- or nitro-substituted phenyl or benzyl.

$R^4$ and $R^5$ independently of one another each very particularly preferably represent respectively optionally fluorine- or chlorine-substituted $C_1$–$C_4$-alkyl, $C_1$–$C_4$-alkoxy, $C_1$–$C_4$-alkylamino, di-($C_1$–$C_4$-alkyl)amino or $C_1$–$C_4$-alkylthio or represent respectively optionally fluorine-, chlorine-, bromine-, nitro-, cyano-, methyl-, methoxy-, trifluoromethyl- or trifluoromethoxy-substituted phenyl, phenoxy or phenylthio.

$R^6$ and $R^7$ independently of one another each very particularly preferably represent hydrogen, represent respectively optionally fluorine- or chlorine-substituted $C_1$–$C_4$-alkyl, $C_3$–$C_6$-cycloalkyl, $C_1$–$C_4$-alkoxy, $C_3$–$C_4$-alkenyl or $C_1$–$C_4$-alkoxy-$C_2$–$C_4$-alkyl, represent respectively optionally fluorine-, chlorine-, bromine-, methyl-, methoxy- or trifluoromethyl-substituted phenyl or benzyl, or together represent a $C_5$–$C_6$-alkylene radical in which optionally one methylene group is replaced by oxygen or sulphur.

The general or preferred radical definitions or illustrations listed above can be combined with each other at will, i.e. combinations between the given ranges and preferred ranges are also possible. These radical definitions or illustrations are valid both for the end products and, in a corresponding manner, for the starting materials and intermediates.

Preference according to the invention is given to those compounds of the formula (I) which contain a combination of the definitions listed above as being preferred (preferable).

Particular preference according to the invention is given to those compounds of the formula (I) which contain a combination of the definitions listed above as being particularly preferred.

Very particular preference according to the invention is given to those compounds of the formula (I) which contain a combination of the definitions listed above as being very particularly preferred.

Saturated or unsaturated hydrocarbon radicals such as alkyl or alkenyl may be, including in combination with hetero atoms such as in alkoxy, straight-chain or branched in each case as far as this is possible.

Optionally substituted radicals may be mono- or polysubstituted, it being possible for the substituents in the case of polysubstitution to be identical or different.

Using, for example, 2-bromoacetophenone and 2-chlorocarbonyl-2-[2-fluoro-4-trifluoromethyl)-phenyl]-ketene as starting materials, the course of the reaction in process (A) according to the invention can be represented by the following equation:

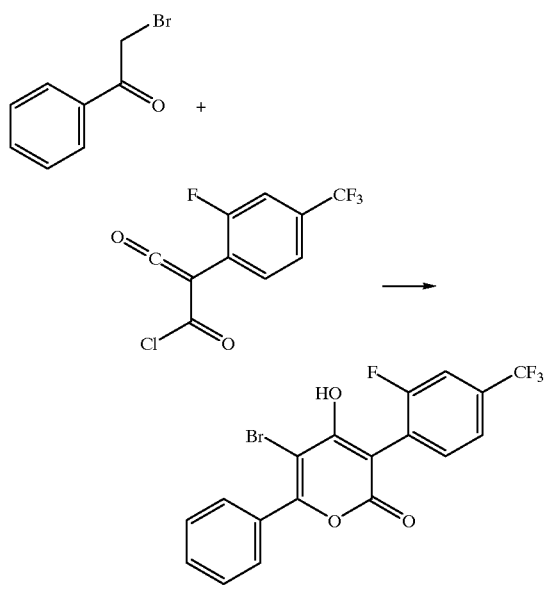

Using, for example, 5-chloro-3-(4-methoxy-6-methyl-phenyl)-4-hydroxy-6-methyl-2-pyrone and pivaloyl chloride as starting materials, the course of the reaction in process (B), variant (α), according to the invention can be represented by the following equation:

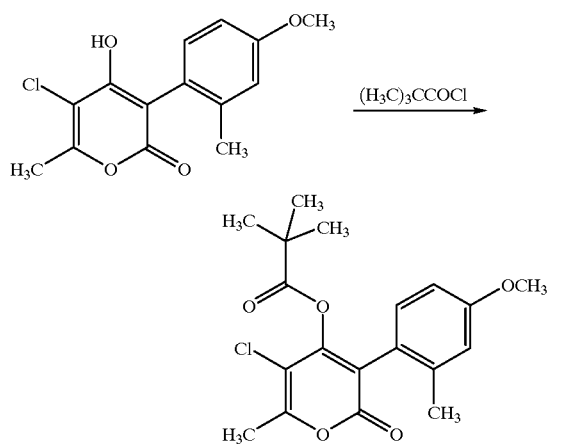

Using, for example, 6-(2-acetyloxy-2-propyl)-5-chloro-3-(2,4,6-trimethyl-phenyl)-4-hydroxy-2-pyrone and acetic anhydride as starting materials, the course of the reaction in process (B), variant (β), according to the invention can be represented by the following equation:

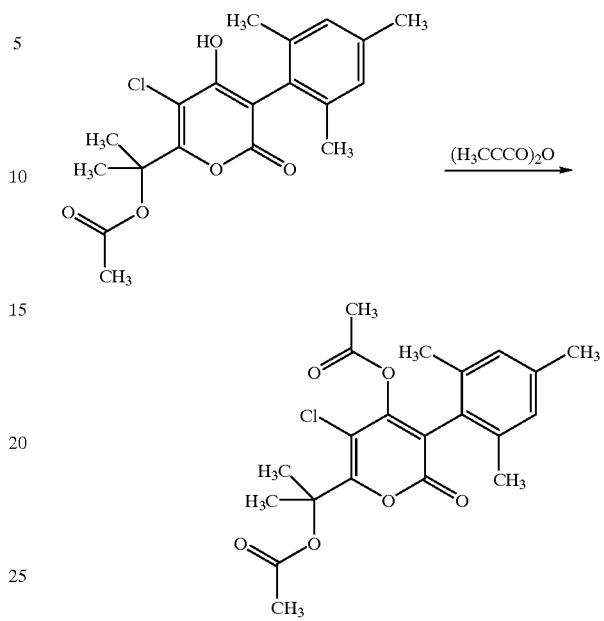

Using, for example, 5-chloro-6-methoxymethyl-3-(2,4-dimethyl-phenyl)-4-hydroxy-2-pyrone and ethoxyethyl chloroformate as starting materials, the course of the reaction in process (C) according to the invention can be represented by the following equation:

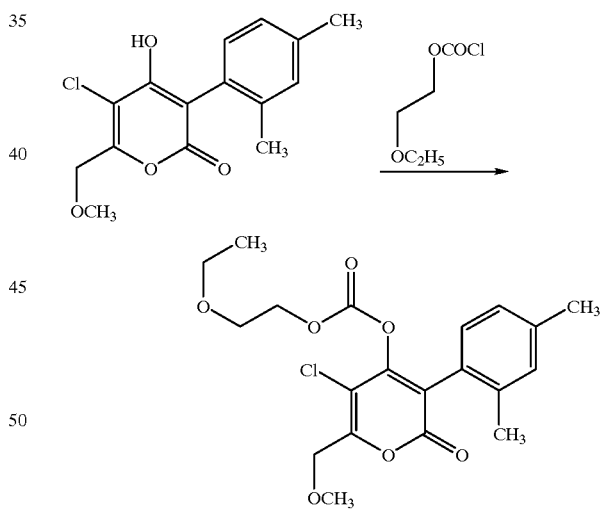

Using, for example, 5-chloro-3-[4-(3-propenyloxy)-2-methyl-phenyl]-4-hydroxy-6-(3-pyridyl)-2-pyrone and methyl chloromonothioformate as starting materials, the course of the reaction in process (D), variant (α), can be represented by the following equation:

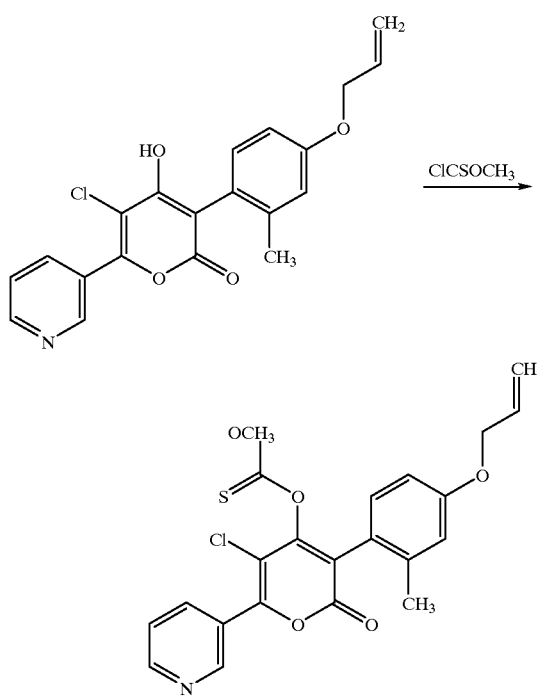

Using, for example, 5-chloro-3-(2-chloro-4,6-dimethyl-phenyl)-4-hydroxy-6-(2-methoxycarbonyl-2-propyl)-2-pyrone, carbon disulphide and methyl iodide as starting materials, the course of the reaction in process (D), variant (β), according to the invention can be represented by the following equation:

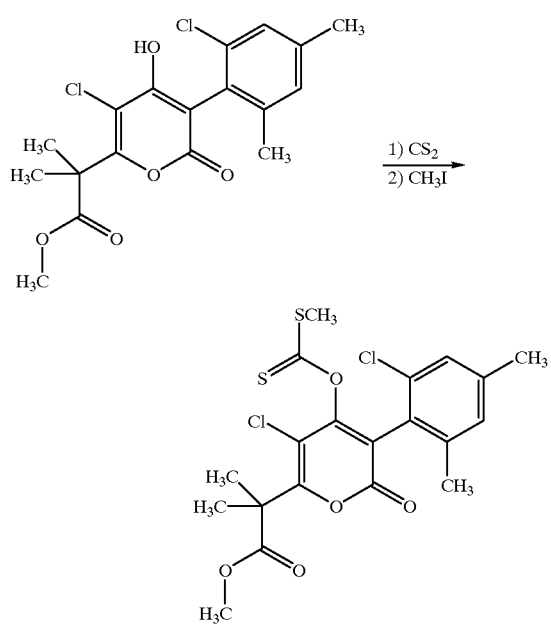

Using, for example, 5-fluoro-3-[4-(4,6-dimethyl-2-bromo-phenyl)-4-hydroxy-6-methyl]-2-pyrone and methanesulfonyl chloride as starting materials, the course of the reaction in process (E) according to the invention can be represented by the following equation:

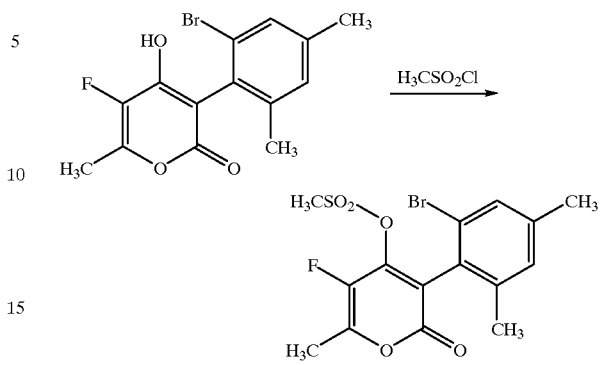

Using, for example, 5-chloro-3-(2-methoxy-4-methyl-phenyl)-4-hydroxy-6-thienyl-2-pyrone and 2,2,2-trifluoroethyl chloromethanethiophosphonate as starting materials, the course of the reaction in process (F) according to the invention can be represented by the following equation:

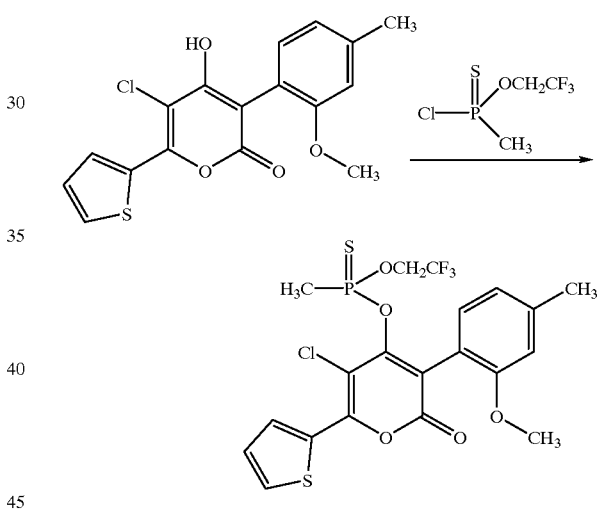

Using, for example, 3-(4-tert-butyl-2-methyl-phenyl)-6-cyclopropyl-5-fluoro-4-hydroxy-2-pyrone and sodium hydroxide as starting materials, the course of the reaction in process (G) according to the invention can be represented by the following equation:

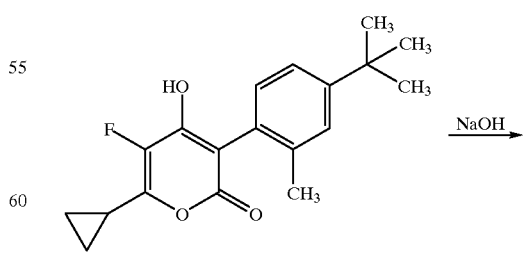

-continued

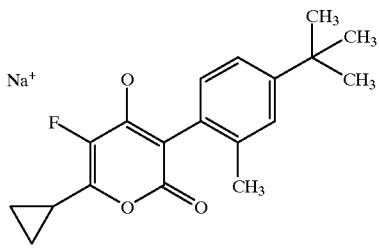

Using, for example, 3-(2-chloro-4-methyl-phenyl)-6-cyclohexyl-5-fluoro-4-hydroxy-2-pyrone and ethyl isocyanate as starting materials, the course of the reaction in process (H), variant (α), according to the invention can be represented by the following equation:

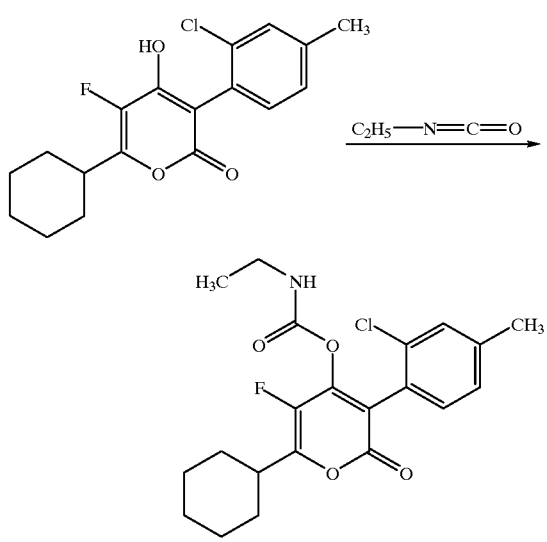

Using, for example, 5-chloro-3-(2,4-dichloro-6-methyl-phenyl)-6-ethyl-4-hydroxy-2-pyrone and dimethylcarbamoyl chloride as starting materials, the course of the reaction in process (H), variant (β), according to the invention can be represented by the following equation:

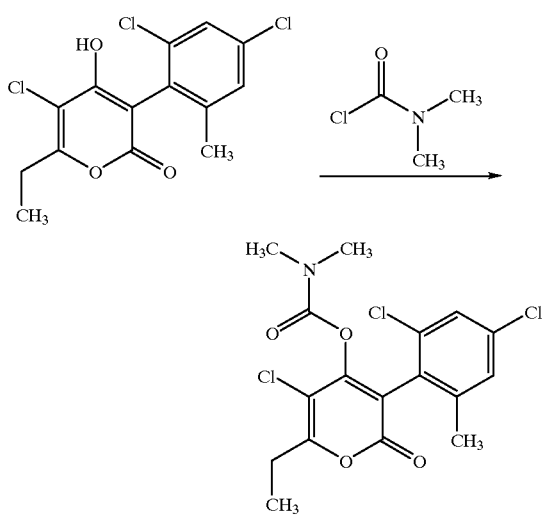

Some of the halogenocarbonyl ketens of the formula (III) required as starting materials for the process (A) are novel and the subject of an earlier, but non-prior-published Application of the Applicant (German Patent Application 195 04 621.8). They can be prepared in a simple manner by methods known in principle (cf. for example Org. Prep. Proced. Int., 7, (4), 155–158, 1975, DE-1 945 703 and EP-508 126). The compounds of the formula (III)

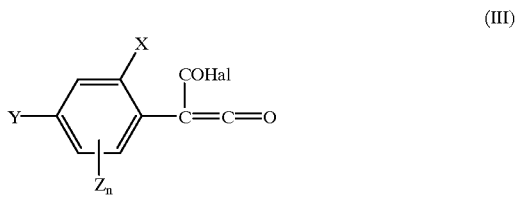
(III)

in which
X, Y, Z and n are each as defined above and
Hal represents chlorine or bromine
are obtained when
substituted phenylmalonic acids of the formula (XV)

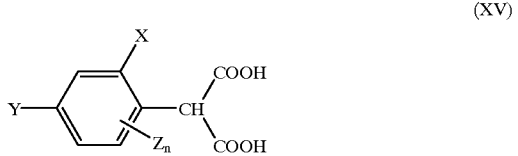
(XV)

in which
X, Y, Z and n are each as defined above
are reacted with acyl halides such as, for example, thionyl chloride, phosphorus(V) chloride, phosphorus(III) chloride, oxalyl chloride, phosgene or thionyl bromide, if appropriate in the presence of catalysts such as, for example, diethylformamide, methylstearyl formamide or triphenylphosphine and, if appropriate, in the presence of bases such as, for example, pyridine or triethylamine, at a temperature between −20° C. and 200° C., preferably between 0° C. and 150° C.

Some of the substituted phenylmalonic acids of the formula (XV) are known and described in the non-prior-published German Patent Application 195 04 621.8 of the Applicant. However, they can be prepared in a simple manner by known processes (cf. for example Organikum, VEB Deutscher Verlag der Wissenschaften, Berlin 1977. p. 517 ff. and EP-508 126).

The carbonyl compounds of the formula (II)

(II)

in which
A and D are as defined above
and which are required as starting materials for the process (A) according to the invention are compounds which are commercially available, generally known or obtainable by known processes.

The acyl halides of the formula (IV), carboxylic anhydrides of the formula (V), chloroformic acid esters or chloroformic acid thioesters of the formula (VI), chloromonothioformic acid esters or chlorodithioformic acid esters of the formula (VII), alkyl halides of the formula (VIII), sulphonyl chlorides of the formula (IX), phosphorus compounds of the formula (X) and metal hydroxides, metal alkoxides or amines of the formulae (XI) and (XII), isocyanates of the formula (XIII) and carbamoyl chlorides of the formula (XIV) required as starting materials for carrying out the processes (B), (C), (D), (E), (F), (G) and (H) according to the invention are generally known compounds of organic or inorganic chemistry.

Process (A) according to the invention is characterized in that carbonyl compounds of the formula (II) are reacted with ketene acid halides of the formula (III), if appropriate in the presence of a diluent and if appropriate in the presence of an acid acceptor.

Diluents which can be used for the process (A) according to the invention are all organic solvents which are inert to the reaction participants. Those preferably utilizable are hydrocarbons, such as o-dichlorobenzene, tetraline, toluene and xylene, furthermore ethers, such as dibutyl ether, glycol dimethyl ether and diglycol dimethyl ether, and additionally polar solvents, such as dimethyl sulphoxide, sulpholane, dimethylformamide or N-methyl-pyrrolidone.

Acid acceptors which can be used when carrying out process (A) according to the invention are all customary acid acceptors.

Those preferably utilizable are tertiary amines, such as triethylamine, pyridine, diazabicyclooctane (DABCO), diazabicycloundecene (DBU), diazabicyclononene (DBN), Hünig base or N,N-dimethyl-aniline.

When carrying out process (A) according to the invention, the reaction temperature can be varied within a relatively wide range. The reaction is expediently carried out at temperatures between 0° C. and 250° C., preferably between 50° C. and 220° C.

Process (A) according to the invention is preferably carried out under atmospheric pressure.

When carrying out process (A) according to the invention, the reaction components of the formulae (II) and (III) and, if appropriate, the acid acceptor are in general employed in approximately equimolar amounts. However, it is also possbile to use one component or the other in a relatively large excess (up to 5 mol).

Process (Bα) is characterized in that compounds of the formula (I-a) are reacted with carboxylic acid halides of the formula (IV), if appropriate in the presence of a diluent and if appropriate in the presence of an acid-binding agent.

Diluents which can be used for the process (Bα) according to the invention are all solvents which are inert to the acid halides. Those preferably utilizable are hydrocarbons, such as benzine, benzene, toluene, xylene and tetraline, furthermore halogenated hydrocarbons, such as methylene chloride, chloroform, carbon tetrachloride, chlorobenzene and o-dichlorobenzene, and also ketones, such as acetone and methyl isopropyl ketone, furthermore ethers, such as diethyl ether, tetrahydrofuran and dioxan, moreover carboxylic acid esters, such as ethyl acetate, nitriles such as acetonitrile and also strongly polar solvents, such as dimethylformamide, dimethylsulphoxide and sulpholane. If the stability to hydrolysis of the acid halide permits, the reaction can also be carried out in the presence of water.

Suitable acid-binding agents in the reaction of process (Bα) according to the invention are all customary acid acceptors. Those preferably utilizable are tertiary amines, such as triethylamine, pyridine, diazabicyclooctane (DABCO), diazabicycloundecene (DBU), diazabicyclonon-ene (DBN), Hünig base and N,N-dimethyl-aniline, furthermore alkaline earth metal oxides, such as magnesium oxide and calcium oxide, and also alkali metal and alkaline earth metal carbonates, such as sodium carbonate, potassium carbonate and calcium carbonate and also alkali metal hydroxides such as sodium hydroxide and potassium hydroxide.

The reaction temperature in the process (Bα) according to the invention can be varied within a relatively wide range. In general, the reaction is carried out at temperatures between –20° C. and +150° C., preferably between 0° C. and 100° C.

When carrying out process (Bα) according to the invention, the starting material of the formula (I-a) and the carboxylic acid halide of the formula (IV) are in general each used in approximately equivalent amounts. However, it is also possible to employ the carboxylic acid halide in a relatively large excess (up to 5 mol). Work-up is carried out according to customary methods.

Process (Bβ) is characterized in that compounds of the formula (I-a) are each reacted with carboxylic anhydrides of the formula (V), if appropriate in the presence of a diluent and if appropriate in the presence of an acid-binding agent.

Diluents which can be used for the process (Bβ) according to the invention are preferably those diluents which are also preferred when using acid halides. Otherwise, a carboxylic anhydride employed in excess may also simultaneously function as diluent.

Possible acid-binding agents added in process (Bβ) are preferably those acid-binding agents that are also preferred when using acid halides.

The reaction temperature in the process (Bβ) according to the invention can be varied within a relatively wide range. In general, the reaction is carried out at temperatures between –20° C. and +150° C., preferably between 0° C. and 100° C.

When carrying out process (Bβ) according to the invention, the starting material of the formula (I-a) and the carboxylic anhydride of the formula (V) are in general each used in approximately equivalent amounts. However, it is also possible to employ the carboxylic anhydride in a relatively large excess (up to 5 mol). Work-up is carried out according to customary methods.

In general, a procedure is used in which diluent and excess carboxylic anhydride and the resulting carboxylic acid are removed by distillation or by washing with an organic solvent or with water.

Process (C) is characterized in that compounds of the formula (I-a) are reacted with chloroformic acid esters or chloroformic acid thioesters of the formula (VI), if appropriate in the presence of a diluent and if appropriate in the presence of an acid-binding agent.

Suitable acid-binding agents for process (C) according to the invention are all customary acid acceptors. Those preferably utilizable are tertiary amines, such as triethylamine, pyridine, DABCO, DBU, DBA, Hünig base and N,N-dimethyl-aniline, furthermore alkaline earth metal oxides, such as magnesium oxide and calcium oxide, additionally alkali metal and alkaline earth metal carbonates, such as sodium carbonate, potassium carbonate and calcium carbonate and also alkali metal hydroxides such as sodium hydroxide and potassium hydroxide.

Diluents which can be used for the process (C) according to the invention are all solvents which are inert to the chloroformic acid esters or chloroformic acid thioesters. Those preferably utilizable are hydrocarbons, such as benzine, benzene, toluene, xylene and tetraline, furthermore halogenated hydrocarbons, such as methylene chloride, chloroform, carbon tetrachloride, chlorobenzene and o-dichlorobenzene, additionally ketones, such as acetone and methyl isopropyl ketone, furthermore ethers, such as diethyl ether, tetrahydrofuran and dioxane, nitriles, such as acetonitrile, moreover carboxylic acid esters, such as ethyl acetate, and also strongly polar solvents, such as dimethylformamide, dimethyl sulphoxide and sulpholane.

When carrying out process (C) according to the invention, the reaction temperature can be varied within a relatively wide range. The reaction temperature is generally between −20° C. and +100° C., preferably between 0° C. and 50° C.

Process (C) according to the invention is in general carried out under atmospheric pressure.

When carrying out process (C) according to the invention, the starting material of the formula (I-a) and the appropriate chloroformic acid ester or chloroformic acid thioester of the formula (VI) are in general each used in approximately equivalent amounts. However, it is also possible to employ one component or the other in a relatively large excess (up to 2 mol). Work-up is carried out according to customary methods. In general, a procedure is used in which precipitated salts are removed and the reaction mixture which remains is concentrated by stripping off the diluent.

Process (D) according to the invention is characterized in that compounds of the formula (I-a) are in each case reacted with (Dα) compounds of the formula (VII) in the presence of a diluent and, if appropriate, in the presence of an acid-binding agent, or (Dβ) carbon disulphide and subsequently with alkyl halides of the formula (VIII), if appropriate in the presence of a diluent and if appropriate in the presence of a base.

In preparation process (Dα), about 1 mol of chloromonothioformic acid ester or chlorodithioformic acid ester of the formula (VII) is reacted per mole of a starting material of the formula (I-a), at 0 to 120° C., preferably at 20 to 60° C.

Diluents which may be added, if appropriate, are all inert polar organic solvents, such as ethers, amides, carboxylic esters, nitriles, sulphones, sulphoxides, and also halogenoalkanes.

Dimethyl sulphoxide, ethyl acetate, acetonitrile, tetrahydrofuran, dimethylformamide or methylene chloride are preferably employed.

If, in a preferred embodiment, the enolate salt of the compound (I-a) is prepared by addition of strong deprotonating agents, for example sodium hydride or potassium tert-butoxide, the further addition of acid-binding agents can be dispensed with.

If acid-binding agents are used, customary inorganic or organic bases are suitable; sodium hydroxide, sodium carbonate, potassium carbonate, pyridine and triethylamine may be mentioned by way of example.

The reaction can be carried out at atmospheric pressure or at elevated pressure; it is preferably carried out at atmospheric pressure. Work-up takes place according to customary methods.

In preparation process (Dβ), the equimolar amount or an excess of carbon disulphide is added per mole of the starting material of the formula (I-a). Here, the reaction is preferably carried out at temperatures from 0 to 50° C., and in particular at 20 to 30° C.

Often, it is advantageous to prepare initially the corresponding salt from the compound of the formula (I-a) by addition of a base (such as, for example, potassium tert-butoxide or sodium hydride). The compound (I-a) is reacted with carbon disulphide until the formation of the intermediate has ended, for example after stirring for several hours at room temperature.

Bases which can be used for the process (Dβ) are all customary proton acceptors. Preference is given to using alkali metal hydrides, alkali metal alkoxides, alkali metal or alkaline earth metal carbonates or bicarbonates or nitrogen bases. Examples include sodium hydride, sodium methoxide, sodium hydroxide, calcium hydroxide, potassium carbonate, sodium bicarbonate, triethylamine, dibenzylamine, diisopropylamine, pyridine, quinoline, diazabicyclooctane (DABCO), diazabicyclononene (DBN) and diazabicycloundecene (DBU).

Diluents which can be used for this process are all customary solvents.

Preference is given to using aromatic hydrocarbons such as benzene or toluene, alcohols such as methanol, ethanol, isopropanol or ethylene glycol, nitrites such as acetonitrile, ethers such as tetrahydrofuran or dioxane, amides such as dimethylformamide and other polar solvents such as dimethyl sulphoxide or sulpholane.

The further reaction with the alkyl halide of the formula (VIII) is preferably carried out at from 0 to 70° C., and in particular at 20 to 50° C. Here, at least an equimolar amount of alkyl halide is employed.

The reaction is carried out at atmospheric pressure or at elevated pressure, preferably at atmospheric pressure.

Work-up is again carried out by customary methods.

Process (E) according to the invention is characterized in that compounds of the formula (I-a) are in each case reacted with sulphonyl chlorides of the formula (IX), if appropriate in the presence of a diluent and if appropriate in the presence of an acid-binding agent.

In preparation process (E), about 1 mol of sulphonyl chloride of the formula (IX) is reacted per mole of starting material of the formula (I-a) at −20 to 1 50° C., preferably at 20 to 70° C.

Process (E) is preferably carried out in the presence of a diluent.

Suitable diluents are all inert polar organic solvents, such as ethers, amides, nitrites, sulphones, sulphoxides or halogenated hydrocarbons.

Dimethyl sulphoxide, tetrahydrofuran, dimethylformamide and methylene chloride are preferably employed.

If, in a preferred embodiment, the enolate salt of the compound (I-a) is prepared by addition of strong deprotonating agents (for example sodium hydride or potassium tert-butoxide), the further addition of acid-binding agents can be dispensed with.

If acid-binding agents are employed, customary inorganic or organic bases are suitable; sodium hydroxide, sodium carbonate, potassium carbonate, pyridine and triethylamine may be mentioned by way of example.

The reaction can be carried out at atmospheric pressure or at elevated pressure; it is preferably carried out at atmospheric pressure. Work-up takes place according to customary methods.

The process (F) according to the invention is characterized in that compounds of the formula (I-a) are in each case reacted with phosphorus compounds of the formula (X), if appropriate in the presence of a diluent and if appropriate in the presence of an acid-binding agent.

In preparation process (F), 1 to 2, preferably 1 to 1.3, mol of the phosphorus compound of the formula (X) is reacted per mole of the compound (I-a) at temperatures between −40° C. and 150° C., preferably between −10° C. and 110° C., to give compounds of the formula (I-e).

The process (F) is preferably carried out in the presence of a diluent.

Suitable diluents are all inert polar organic solvents, such as halogenated hydrocarbons, carboxylic acid esters, ethers, amides, nitrites, sulphones, sulphoxides, etc.

Acetonitrile, dimethyl sulphoxide, tetrahydrofuran, dimethylformamide or methylene chloride are preferably employed.

Acid-binding agents which may be added, if appropriate, are customary inorganic or organic bases, such as hydroxides, carbonates or amines. By way of example, sodium hydroxide, sodium carbonate, potassium carbonate, pyridine and triethylamine may be mentioned.

The reaction may be carried out at atmospheric pressure or at elevated pressure; it is preferably carried out at atmospheric pressure. Work-up takes place according to conventional methods of organic chemistry. The end products are preferably purified by crystallization, chromatographic purification or by so-called "incipient distillation", i.e. removal of the volatile constituents in vacuo.

Process (G) is characterized in that compounds of the formula (I-a) are reacted with metal hydroxides or metal alkoxides of the formula (XI) or amines of the formula (XII), if appropriate in the presence of a diluent.

Diluents which can be used for process (G) according to the invention are preferably ethers such as tetrahydrofuran, dioxane and diethyl ether or else alcohols such as methanol, ethanol and isopropanol, but also water. Process (G) according to the invention is generally carried out under atmospheric pressure. The reaction temperature is in general between –20° C. and 100° C., preferably between 0° C. and 50° C.

Process (H) according to the invention is characterized in that compounds of the formula (I-a) are reacted with (Hα) compounds of the formula (XIII), if appropriate in the presence of a diluent and if appropriate in the presence of a catalyst, or (Hβ) with compounds of the formula (XIV), if appropriate in the presence of a diluent and if appropriate in the presence of an acid-binding agent.

In preparation process (Hα), about 1 mol of isocyanate of the formula (XIII) is reacted per mole of starting material of the formula (I-a) at 0 to 100° C., preferably at 20 to 50° C.

Process (Hα) is preferably carried out in the presence of a diluent.

Suitable diluents are all inert organic solvents, such as ethers, amides, nitriles, sulphones or sulphoxides.

Catalysts may, if desired, be added to accelerate the reaction. The catalysts employed can very advantageously be organotin compounds, for example dibutyltin dilaurate.

The reaction is preferably carried out at atmospheric pressure.

In preparation process (Hβ), about 1 mol of carbamoyl chloride of the formula (XIV) is reacted at 0 to 150° C., preferably at 20 to 70° C., per mole of starting material of the formula (I-a).

Possible diluents optionally added are all inert polar organic solvents, such as ethers, carboxylic acid esters, nitrites, amides, sulphones, sulphoxides or halogenated hydrocarbons.

Dimethyl sulphoxide, tetrahydrofuran, dimethylformamide or methylene chloride are preferably employed.

If, in a preferred embodiment, the enolate salt of the compound (I-a) is prepared by addition of strong deprotonating agents (e.g. sodium hydride or potassium tert-butoxide), the further addition of acid-binding agents can be dispensed with.

If acid-binding agents are employed, customary inorganic or organic bases are suitable; those which may be mentioned by way of example are sodium hydroxide, sodium carbonate, potassium carbonate, triethylamine or pyridine.

The reaction can be carried out at atmospheric pressure or at elevated pressure, preferably at atmospheric pressure. Work-up takes place according to customary methods.

The compounds according to the invention, having good crop tolerance and favourable homeotherm safety, are suitable for controlling animal pests, preferably arthropods and nematodes, in particular insects and arachnids, which are encountered in agriculture, in forestry, in the protection of stored products and of materials, and in the hygiene sector. They are active against normally sensitive and resistant species and against all or some stages of development. The abovementioned pests include:

From the order of Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera spec.*

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.*

From the order of the Dernaptera, for example, *Forficula auricularia.*

From the order of the Isoptera, for example, Reticulitermes spp.

From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Acanthoscelides obtectus, Hylotrupes bajulus, Agelastica alni, Leptinotarsa decemlineata, Phaedon* cochleariae, Diabrotica spp., *Psylliodes chrysocephala, Epilachna varive stis*, Atomaria spp., *Oryzaephilus surinamensis*, Antho nomus spp., Sitophilus spp., *Otiorrhynchus sulcatus, Cosmopolites sordidus, Ceuthorrhynchus assimilis, Hypera postica*, Dermestes spp., Trogoderna spp., Anthrenus spp., Attagenus spp., Lyctus spp., *Meligethes aeneus*, Ptinus spp., *Niptus hololeucus, Gibbium psylloides*, Tribolium spp., *Tenebrio molitor*, Agriotes spp., Cono derus spp., *Melolontha melolontha, Amphimallon soisti tialis* and *Costelytra zealandica*.

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae* and *Tipula paludosa*.

From the order of the Siphonaptera, for example, *Xenopsylla cheopis* and Ceratophyllus spp.

From the order of the Arachnida, for example, *Scorpio maurus* and *Latrodectus mactans*.

From the order of the Acarina, for example, *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp. and Tetranychus spp.

The active compounds according to the invention have high insecticidal and acaricidal activity.

Particularly successfully, they can be employed for controlling plant-damaging insects, for example against the larvae of the mustard beetle (*Phaedon cochleariae*), against the caterpillars of the diamond-back moth (*Plutella maculipennis*), against the caterpillars of the owlet moth (*Spodoptera frugiperda*), against the larvae of the green rice leaf hopper (*Nephotettix cincticeps*) or against green peach aphids (*Myzus persicae*) and for controlling plant-damaging arachnids (Acari) such as, for example, against the greenhouse red spider mite (*Tetranychus urticae*).

The active compounds according to the invention can furthermore be used as defoliants, desiccants, haulm-killers and, especially, as weed-killers. By weeds, in the broadest sense, are to be understood all plants which grow in locations where they are undesired. Whether the substances according to the invention act as total or selective herbicides depends essentially on the amount used.

The dosages of the active compounds according to the invention required for weed control are between 0.001 and 10 kg/ha, preferably between 0.005 and 5 kg/ha.

The active compounds according to the invention can be used, for example, in connection with the following plants: Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotola, Lindemia, Lamium, Veronica, Abutilon, Emex, Datura, Viola, Galeopsis, Papaver, Centaurea, Trifolium, Ranunculus and Taraxacum.

Dicotyledonous crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cycnodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledonous crops of the genera: Oryza, Zea, Triticum, Hordeum, Avena, Secale, Sorghum, Panicum, Sachharum, Ananas, Asparagus and Allium.

However, the use of the active compounds according to the invention is in no way restricted to these genera, but also extends in the same manner to other plants.

The compounds are suitable, depending on the concentration, for the total control of weeds, for example on industrial terrain and rail tracks, and on paths and squares with or without tree plantings. Equally, the compounds can be employed for controlling weeds in perennial cultures, for example forests, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pasture-land, and for the selective control of weeds in annual crops.

The active compounds according to the invention are particularly suitable for the selective control of weeds by the pre-emergence method. For example, they can be used very successfully for controlling harmful grasses in barley and soya.

At the appropriate application rates, the compounds according to the invention also exhibit fungicidal activity, in particular against *Pyricularia oryzae* in rice.

The active compounds can be converted into the customary formulations, such as solutions, emulsions, wettable powders, suspensions, powders, dusting agents, pastes, soluble powders, granules, suspo-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers.

If the extender used is water, it is also possible to employ for example organic solvents as auxiliary solvents. Essentially, suitable liquid solvents include: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol and their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are:
for example ammonium salts and ground natural minerals, such as kaolins, clays, talc, chalk, quartz, attapulgite, montmorillonite or diatomaceous earth, and ground synthetic minerals, such as finely divided silica, alumina and silicates, suitable solid carriers for granules are: for example crushed and fractionated natural rocks such as calcite, marble, pumice, sepiolite and dolomite, and synthetic granules of inorganic and organic meals, and granules of organic material such as sawdust, coconut shells, maize cobs and tobacco stalks;

suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersing agents are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, and natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%.

The active compound according to the invention may be present in the form of its commercially available formulations and in the use forms prepared from these formulations, as a mixture with other active compounds, such as insecticides, attractants, sterilants, acaricides, nematicides, fungicides, growth regulators or herbicides. The insecticides include, for example, phosphoric esters, carbamates, carboxylic esters, chlorinated hydrocarbons, phenylureas, compounds produced by microorganisms, etc.

Particularly advantageous mixing partners are, for example, those listed below:

Fungicides:
2-aminobutane; 2-anilino-4-methyl-6-cyclopropyl-pyrimidine; 2',6'-dibromo-2-methyl-4'-trifluoromethoxy-4'-trifluoro-methyl-1,3-thiazole-5-carboxanilide; 2,6-dichloro-N-(4-trifluoromethylbenzyl)-benzamide; (E)-2-methoxyimino-N-methyl-2-(2-phenoxyphenyl)-acetamide; 8-hydroxyquinoline sulphate; methyl (E)-2-{2-[6-(2-cyanophenoxy)-pyrimidin-4-yloxy]-phenyl}-3-methoxyacrylate; methyl (E)-methoximino-[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulphamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulphocarb, methfuroxam, metiram, metsulphovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, phthalide, pimaricin, piperalin, polycarbamates, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforin, triticonazole, validamycin A, vinclozolin, zineb, ziram.

Bactencides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:
abamectin, abamectin, AC 303 630, acephate, acrinathrin, alanycarb, aldicarb, alphamethirin, amitraz, avermectin, AZ 60541, azadirachtin, azinphos A, azinphos M, azocyclotin.

Bacillus thuringiensis, bendiocarb, benfuracarb, bensultap, beta-cyluthrin, bifenthrin, BPMC, brofenprox, bromophos A, bufencarb, buprofezin, butocarboxin, butylpyridaben, cadusafos, carbaryl, carbofuran, carbophenothion, carbosulphan, cartap, CGA 157 419, CGA 184699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypernethrin, cyromazine, deltamethrin, demeton-M, demeton-S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivemectin, lamda-cyhalothrin, lufenuron, malathion, mecarbam, mervinphos, mesulfenphos, metaldehyde, methacrifos, methamidophos, methidathion, methiocarb, methomyl, metoicarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamdon, phoxim, pirimicarb, pirimiphos M, pirimiphos A, profenofos, promecarb, propaphos, propoxur, prothiofos, prothoate, pymetrozin, pyrachlophos, pyradaphenthion, pyresmethrin, pyrethrum, pyridaben, pyrimidifen, pyriproxifen, quinalphos, RH 5992, salithion, sebufos, silafluofen, sulfotep, sulprofos, tebufenozid, tebufenpyrad, tebupirimphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, YI 5301/5302, zetamethrin.

Herbicides:

for example anilides such as, for example, diflufenican and propanil; arylcarboxylic acids such as, for example, dichloropicolinic acid, dicamba and picloram; aryloxy-alkanoic acids such as, for example, 2,4-D, 2,4-DB, 2,4-DP, fluroxypyr, MCPA, MCPP and triclopyr; aryloxy-phenoxy-alkanoic esters such as, for example, diclofopmethyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulphonylureas such as, for example, amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron and tribenuron-methyl; thiolcarbamates such as, for example, butylate, cycloate, di-allate, EPTC, esprocarb, molinate, prosulfocarb, thiobencarb and triallate; triazines such as, for example, atrazine, cyanazine, simazine, simetryne, terbutryne and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

The active compound according to the invention can furthermore be present in its commercially available formulations and in the use forms prepared from these formulations, as a mixture with synergists. Synergists are compounds which increase the action of the active compounds without it being necessary for the synergist added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compound has an excellent residual action on wood and clay as well as a good stability to alkali on limed substrates.

The active compounds according to the invention are not only active against plant, hygiene and stored-product pests, but also, in the veterinary medicine sector, against animal parasites (ectoparasites), such as ixodid ticks, argasid ticks, scab mites, trombiculid mites, flies (stinging and sucking), parasitic fly larvae, lice, hair lice, bird lice and fleas. These parasites include:

From the order of the Anoplurida, for example, Haematopinus spp., Linognathus spp., Pediculus spp., Phtirus spp., Solenopotes spp.

From the order of the Mallophagida and the sub-orders Amblycerina and Ischnocerina, for example, Trimenopon spp., Menopon spp., Trinoton spp., Bovicola spp., Wemeckiella spp., Lepikentron spp., Damalina spp., Trichodectes spp., Felicola spp.

From the order Diptera and the sub-orders Nematocerina and Brachycerina, for example, Aedes spp., Anopheles spp., Culex spp., Simulium spp., Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophaga spp., Oestrus spp., Hypoderma spp., Gasterophilus spp., Hippobosca spp., Lipoptena spp. and Melophagus spp.

From the order of the Siphonapterida, for example, Pulex spp., Ctenocephalides spp., Xenopsylla spp. and Ceratophyllus spp.

From the order of the Heteropterida, for example, Cimex spp., Triatoma spp., Rhodnius spp. and Panstrongylus spp.

From the order of the Blattarida, for example, *Blatta orientalis, Periplaneta americana, Blattela germanica* and Supella spp.

From the sub-class of the Acaria (Acarida) and the orders of the Meta- and

Mesostigmata, for example Argas spp., Ornithodorus spp., Otobius spp., Ixodes spp., Amblyomma spp., Boophilus spp., Dermacentor spp., Haemophysalis spp., Hyaloinma spp., Rhipicephalus spp., Dermanyssus spp., Raillietia spp., Pneumonyssus spp., Sternostoma spp. and Varroa spp.

From the order of the Actinedida (Prostigmata) and Acaridida (Astigmata), for example Acarapis spp., Cheyletiella spp., Ornithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Octodectes spp., Sarcoptes spp., Notoedres spp., Knemidocoptes spp., Cytodites spp. and Laminosioptes spp.

The active compounds of the formula (I) according to the invention are also suitable for controlling arthropods which attack agricultural livestock, such as, for example, cattle, sheep, goats, horses, pigs, donkeys, camels, buffalo, rabbits, chickens, turkeys, ducks, geese, honey bees, other domestic animals, such as, for example, dogs, cats, cage birds, aquarium fish, and so-called experimental animals such as, for example, hamsters, guinea-pigs, rats and mice. By controlling these arthropods, it is intended to reduce mortality and decreased performance (in meat, milk, wool, hides, eggs, honey and the like), so that more economical and simpler animal keeping is made possible by using the active compounds according to the invention.

In the veterinary sector, the active compounds according to the invention are used in a known manner by enteral administration, for example in the form of tablets, capsules, drinks, drenches, granules, pastes, boluses, the feed-through method, suppositories, by parenteral administration, such as, for example, by means of injections (intramuscular, subcutaneous, intravenous, intraperitoneal and the like), implants, by nasal application, by dermal administration, for example in the form of dipping or bathing, spraying, pouring-on and spotting-on, washing, dusting, and with the aid of shaped articles which comprise active compound, such as collars, ear tags, tail marks, limb bands, halters, marking devices and the like.

When administered to livestock, poultry, domestic animals and the like, the active compounds of the formula (I) can be used as formulations (for example powders, emulsions, flowables) which comprise the active compounds in an amount of 1 to 80% by weight, either directly or after dilution by a factor of 100 to 10,000, or they may be used in the form of a chemical bath.

Furthermore, it has been found that the compounds of the formula (1) according to the invention have a potent insecticidal action against insects which destroy industrial materials.

The following insects may be mentioned by way of example and as being preferred, but without any limitation:

Beetles, such as

Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis; Xyleborus spec. Tryptodendron spec. Apate monachus, Bostrychus capucins, Heterobostrychus brunneus, Sinoxylon spec. Dinoderus minutus.

Dermapterans, such as

Sirex juvencus, Urocerus gigas, Urocerus gigas taignus, Urocerus augur.

Termites, such as

Kalotermes flavicollis, Cryptotermes brevis, Heterotermes indicola, Reticulitermes flavipes, Reticulitermes santonensis, Reticuliterrnes lucifugus, Mastotermes darwiniensis, Zootermopsis nevadensis, Coptotermes formosanus;

Bristletails, such as Lepisma saccharina.

Industrial materials are to be understood as meaning, in the present context, non-live materials such as, preferably, synthetic materials, glues, sizes, paper and board, leather, wood and timber products, and paint.

The materials to be very particularly protected against attack by insects are wood and timber products.

Wood and timber products which can be protected by the composition according to the invention or mixtures comprising such a composition are to be understood as meaning, for example, construction timber, wooden beams, railway sleepers, bridge components, jetties, wooden vehicles, boxes, pallets, containers, telephone poles, wood lagging, windows and doors made of wood, plywood, particle board, joiner's articles, or wood products which, quite generally, are used in the construction of houses or in joinery.

The active compounds can be used as such, in the form of concentrates or generally customary formulations, such as powders, granules, solutions, suspensions, emulsions or pastes.

The formulations mentioned can be prepared in a manner known per se, for example by mixing the active compounds with at least one solvent or diluent, emulsifier, dispersant and/or binder or fixative, water repellent, if appropriate desiccants and UV stabilizers and, if appropriate, colorants and pigments and other processing auxiliaries.

The insecticidal compositions or concentrates used for the protection of wood and wooden materials comprise the active compound according to the invention at a concentration of 0.0001 to 95% by weight, in particular 0.001 to 60% by weight.

The amount of the compositions or concentrates employed depends on the species and the occurrence of the insects and on the medium. The optimum rate of application can be determined upon use in each case by test series. However, in general, it suffices to employ 0.0001 to 20% by weight, preferably 0.001 to 10% by weight, of the active compound, based on the material to be protected.

The solvent and/or diluent used is an organochemical solvent or solvent mixture and/or an oily or oil-type organochemical solvent or solvent mixture of low volatility and/or a polar organochemical solvent or solvent mixture and/or water and, if appropriate, an emulsifier and/or wetting agent.

Organochemical solvents which are preferably employed are oily or oil-type solvents having an evaporation number of above 35 and a flashpoint of above 30° C., preferably above 45° C. Substances which are used as such oily and oil-type solvents which have low volatility and are insoluble in water are suitable mineral oils or their aromatic fractions, or mineral-oil-containing solvent mixtures, preferably white spirit, petroleum and/or alkylbenzene.

Substances which are advantageously used are mineral oils with a boiling range of 170 to 220° C., white spirit with a boiling range of 170 to 220° C., spindle oil with a boiling range of 250 to 350° C., petroleum or aromatics of boiling range 160 to 280° C., essence of turpentine and the like.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably α-monochloronaphthalene, are used.

The organic oily or oil-type solvents of low volatility having an evaporation number of above 35 and a flashpoint of above 30° C., preferably above 45° C., can be partially replaced by organochemical solvents of high or medium volatility, with the proviso that the solvent mixture also has an evaporation number of above 35 and a flashpoint of above 30° C., preferably above 45° C., and that the insecticide/fungicide mixture is soluble or emulsifiable in this solvent mixture.

In a preferred embodiment, part of the organochemical solvent or solvent mixture is replaced or an aliphatic polar organochemical solvent or solvent mixture. Substances which are preferably used are aliphatic organochemical solvents having hydroxyl and/or ester and/or ether groups, such as, for example, glycol ether, esters and the like.

The organochemical binders used within the scope of the present invention are the synthetic resins and/or binding drying oils which are known per se and can be diluted with water and/or are soluble or dispersible or emulsifiable in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin, such as indene/coumarone resin, silicone resin, drying vegetable and/or drying oils and/or physically drying binders based on a natural and/or synthetic resin.

The synthetic resin used as the binder can be employed in the form of an emulsion, dispersion or solution. Up to 10% by weight of bitumen or bituminous substances can also be used as binders. In addition, colorants, pigments, water repellents, odour-masking substances and inhibitors or anti-corrosives which are known per se and the like can also be employed.

The composition or the concentrate preferably comprises, in accordance with the invention, at least one alkyd resin or modified alkyd resin and/or a drying vegetable oil as the organochemical binder. Preferably used according to the invention are alkyd resins with an oil content of over 45% by weight, preferably 50 to 68% by weight.

All or some of the abovementioned binder can be replaced by a fixative (mixture) or a plasticizer (mixture). These additives are intended to prevent volatilization of the active compounds and crystallization or precipitation. They preferably replace 0.01 to 30% of the binder (based on 100% of binder employed).

The plasticizers are from the chemical classes of the phthalic esters, such as dibutyl phthalate, dioctyl phthalate or benzylbutyl phthalate, the phosphoric esters, such as tributyl phosphate, the adipic esters, such as di-(2-ethylhexyl) adipate, the stearates, such as butyl stearate or amyl stearate, the oleates, such as butyl oleate, the glycerol ethers or relatively high-molecular-weight glycol ethers, glycerol esters and p-toluenesulphonic esters.

Fixatives are chemically based on polyvinyl alkyl ethers, such as, for example, polyvinyl methyl ether, or ketones, such as benzophenone or ethylene benzophenone.

Also particularly suitable as a solvent or diluent is water, if appropriate as a mixture with one or more of the abovementioned organochemical solvents or diluents, emulsifiers and dispersants.

Particularly effective protection of wood is achieved by large-scale industrial impregnation processes, for example vacuum, double-vacuum or pressure processes.

If appropriate, the ready-to-use compositions can additionally comprise other insecticides and, if appropriate, additionally one or more fungicides.

Suitable additional components which may be admixed are, preferably, the insecticides and fungicides mentioned in WO 94/29 268. The compounds mentioned in that document are expressly incorporated into the present application by reference.

Very particularly preferred components which may be admixed are insecticides, such as chlorpyriphos, phoxim, silafluofin, alphamethrin, cyfluthrin, cypermethrin, deltamethrin, permethrin, imidacloprid, NI-25, flufenoxuron, hexaflumuron and triflumuron, and fungicides, such as epoxyconazole, hexaconazole, azaconazole, propiconazole, tebuconazole, cyproconazole, metconazole, imazalil, dichlorofluanide, tolylfluanide, 3-iodo-2-propinyl-butyl carbamate, N-octyl-isothiazolin-3-one and 4,5-dichloro-N-octylisothiazolin-3-one.

The preparation and the use of the active compounds according to the invention is illustrated by the examples below.

PREPARATION EXAMPLES

Example (I-a-1)

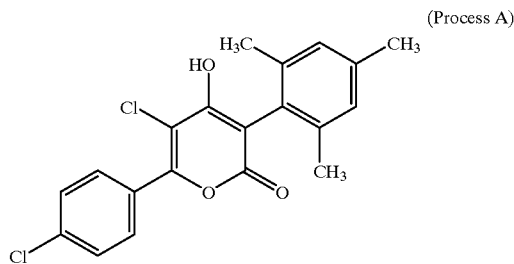

(Process A)

Under exclusion of moisture, 7.6 g (40 mmol) of ω-chloro-4-chloroacetophenone are added to 8.8 g (40 mmol) of mesitylchlorocarbonylketene, and the mixture is heated to 200° C. for 6 h. The reaction product is comminuted using pestle and mortar and digested with toluene. The precipitate is separated off by filtration and dried. 14 g (93% of theory) of 5-chloro-6-(4-chlorophenyl)-4-hydroxy-(2,4,6-trimethylphenyl)-2-pyrone of melting point 229–231° C. are obtained.

Similarly to Example (I-a-1) and/or according to the general preparation instructions, the compounds of the formula (I-a) listed in Table 1 below were obtained.

TABLE 1

(I-a)

| Ex. No. | A | D | X | Y | $Z_n$ | m.p. |
|---|---|---|---|---|---|---|
| I-a-2 | F | $C_6H_5$ | $CH_3$ | $CH_3$ | 6-$CH_3$ | 272–273° C. |
| I-a-3 | F | $C(CH_3)_3$ | $CH_3$ | $CH_3$ | 6-$CH_3$ | 192–194° C. |
| I-a-4 | Cl | $C(CH_3)_3$ | $CH_3$ | $CH_3$ | 6-$CH_3$ | 197–200° C. |
| I-a-5 | Cl | $C(CH_3)_2$—$CH(CH_3)_2$ | $CH_3$ | $CH_3$ | 6-$CH_3$ | 214–217° C. |
| I-a-6 | Cl | 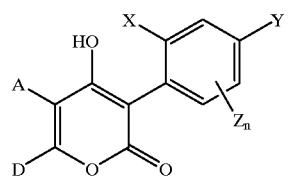 | $CH_3$ | $CH_3$ | 6-$CH_3$ | 110–112° C. |

TABLE 1-continued (I-a)

| Ex. No. | A | D | X | Y | $Z_n$ | m.p. |
|---|---|---|---|---|---|---|
| I-a-7 | Cl | 1-chloro-1-methylcyclopropyl | $CH_3$ | $CH_3$ | 6-$CH_3$ | 100–103° C. |
| I-a-8 | Cl | $C(CH_3)(C_2H_5)$—$(CH_2)_3CH_3$ | $CH_3$ | $CH_3$ | 6-$CH_3$ | 114–116° C. |
| I-a-9 | Cl | $C_6H_5$(=phenyl) | $CH_3$ | $CH_3$ | 6-$CH_3$ | 211–213° C. |
| I-a-10 | Br | $C_6H_5$ | $CH_3$ | $CH_3$ | 6-$CH_3$ | 291–293° C. |
| I-a-11 | Cl | 4-F-$C_6H_4$ | $CH_3$ | $CH_3$ | 6-$CH_3$ | 199–201° C. |
| I-a-12 | Cl | 4-F-$C_6H_4$ | $CH_3$ | $CH_3$ | H | 175–178° C. |
| I-a-13 | Cl | 4-F-$C_6H_4$ | $CH_3$ | H | H | 210–211° C. |
| I-a-14 | Cl | $C(CH_3)_3$ | $CH_3$ | $CH_3$ | H | 140–142° C. |
| I-a-15 | Cl | $C(CH_3)_3$ | Cl | $CH_3$ | 6-Cl | 296–298° C. |
| I-a-16 | Cl | $C(CH_3)_3$ | $CH_3$ | H | H | 71–74° C. |
| I-a-17 | Cl | 4-F-$C_6H_4$ | Cl | Cl | H | 238–240° C. |
| I-a-18 | Cl | $C(CH_3)_3$ | Cl | Cl | H | 296–298° C. |
| I-a-19 | Cl | 4-Cl-$C_6H_4$ | $CH_3$ | $CH_3$ | 6-$CH_3$ | 229–231° C. |
| I-a-20 | Cl | 4-Cl-$C_6H_4$ | $CH_3$ | F | H | 229–231° C. |
| I-a-21 | Cl | $C(CH_3)_3$ | $CH_3$ | Br | 6-$CH_3$ | 250–252° C. |
| I-a-22 | Cl | 4-F-$C_6H_4$ | $CH_3$ | Br | 6-$CH_3$ | 266–268° C. |
| I-a-23 | Cl | 4-F-$C_6H_4$ | $CH_3$ | Cl | H | 254–255° C. |
| I-a-24 | Cl | $C(CH_3)_3$ | $CH_3$ | Cl | H | 117–118° C. |

TABLE 1-continued (I-a)

[Structure: pyrone with substituents A, D, HO, and phenyl ring with X, Y, Z_n]

| Ex. No. | A | D | X | Y | $Z_n$ | m.p. |
|---|---|---|---|---|---|---|
| I-a-25 | Cl | 4-F-phenyl | $CH_3$ | H | 6-$CH_3$ | 235–237° C. |
| I-a-26 | Cl | $C(CH_3)_3$ | $CH_3$ | H | 6-Cl | 196–197° C. |
| I-a-27 | Cl | 4-F-phenyl | Cl | $CH_3$ | H | 252–254° C. |
| I-a-28 | Cl | $C(CH_3)_3$ | Cl | $CH_3$ | H | 192–194° C. |
| I-a-29 | Cl | $C(CH_3)_3$ | $C_2H_5$ | Br | 6-$C_2H_5$ | 181–183° C. |
| I-a-30 | Cl | 4-F-phenyl | $C_2H_5$ | Br | 6-$C_2H_5$ | 184–186° C. |
| I-a-31 | Cl | 4-F-phenyl | Cl | $CH_3$ | 6-$CH_3$ | 234–235° C. |
| I-a-32 | Cl | $C(CH_3)_3$ | Cl | $CH_3$ | 6-$CH_3$ | 276–277° C. |

Example (I-b-1)

(Process Bα)

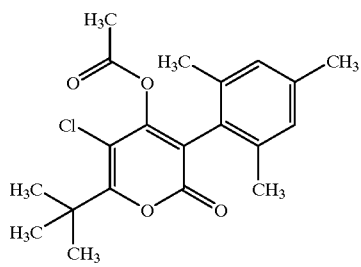

6.4 g (20 mmol) of 6-tert-butyl-5-chloro-4-hydroxy-3-(2,4,6-trimethylphenyl)-2-pyrone (Ex. I-a-4) are initially charged in 50 ml of ethyl acetate. At 20° C., 2.02 g (20 mmol) of triethylamine are added, and at 0° C. a solution of 1.6 g (20 mmol) of acetyl chloride in 20 ml of ethyl acetate is added dropwise. The mixture is subsequently stirred at 20° C. for 20 h. Precipitated triethylamine hydrochloride is filtered off with suction and washed with ethyl acetate. The combined mother liquors are washed twice with 50 ml of half-concentrated sodium chloride solution each time, dried over magnesium sulphate and concentrated under reduced pressure. 7.2 g of crude product are obtained. Flash chromatography over silica gel 60 (35–70 μm) using toluene-:acetone 30:1 as eluent yields 4.1 g (57% of theory) of 4-acetyloxy-6-tert-butyl-5-chloro-(2,4,6-trimethylphenyl)-2-pyrone of melting point 116–118° C.

Similarly to Example (I-b-1) and/or according to the general preparation instructions, the compounds of the formula (I-b) listed in Tables 2 and 2a below were obtained.

TABLE 2
(I-b)
| Ex. No. | A | D | X | Y | $Z_n$ | $R^1$ | m.p. [° C.] |
|---|---|---|---|---|---|---|---|
| I-b-2 | Cl | $C_6H_5$ | $CH_3$ | $CH_3$ | 6-$CH_3$ | $CH_3$ | 132–134 |
| I-b-3 | Cl | $C_6H_5$ | $CH_3$ | $CH_3$ | 6-$CH_3$ | $CH(CH_3)_2$ | 108–110 |
| I-b-4 | Cl | $C_6H_5$ | $CH_3$ | $CH_3$ | 6-$CH_3$ | 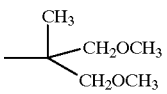 | 150–152 |
| I-b-5 | Cl | $C_6H_5$ | $CH_3$ | $CH_3$ | 6-$CH_3$ | 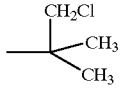 | 121–123 |
| I-b-6 | Cl | $C_6H_5$ | $CH_3$ | $CH_3$ | 6-$CH_3$ | 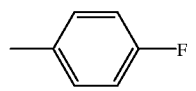 | 91–93 |
| I-b-7 | Cl | 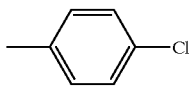 | $CH_3$ | $CH_3$ | 6-$CH_3$ | $CH_3$ | 159–161 |
| I-b-8 | Cl | 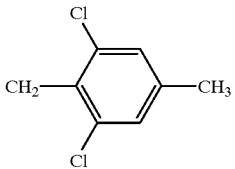 | $CH_3$ | $CH_3$ | 6-$CH_3$ | $CH_3$ | 174–175 |
| I-b-9 | Cl | $C(CH_3)_3$ | Cl | $CH_3$ | 6-Cl | 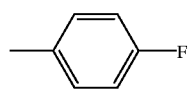 | 64–66 |
| I-b-10 | Cl | 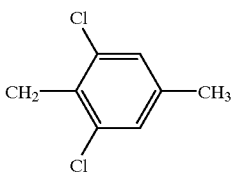 | Cl | $CH_3$ | 6-Cl | 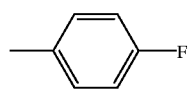 | 96–99 |

TABLE 2a

| Ex. No. | A | D | X | Y | $Z_n$ | $R^1$ | m.p.[° C.] |
|---|---|---|---|---|---|---|---|
| I-b-11 | Cl | $C(CH_3)_3$ | $CH_3$ | $CH_3$ | 6-$CH_3$ | $C(CH_3)_3$ | 149–151 |
| I-b-12 | Cl | $C_6H_5$ | $CH_3$ | $CH_3$ | 6-$CH_3$ | $C(CH_3)_3$ | 175–178 |
| I-b-13 | Cl | 4-Cl-$C_6H_4$ | $CH_3$ | $CH_3$ | 6-$CH_3$ | $C(CH_3)_3$ | 198–199 |
| I-b-14 | Cl | 4-F-$C_6H_4$ | $CH_3$ | $CH_3$ | 6-$CH_3$ | $C(CH_3)_3$ | 154–156 |

Example (I-c-1)

(Process C)

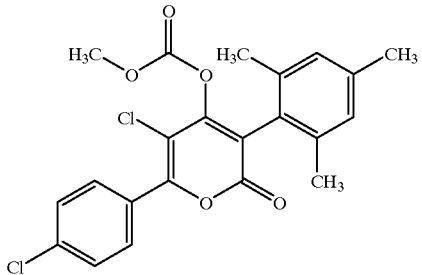

3.8 g (10 mmol) of 5-chloro-6-(4-chlorophenyl)-4-hydroxy-3-(2,4,6-trimethylphenyl)-2-pyrone (Example I-a-1) are initially charged in 25 ml of ethyl acetate. At 20° C., 1.0 g (10 mmol) of triethylamine are added and a solution of 0.95 g (10 mmol) of methyl chloroformate in 10 ml of ethyl acetate is added dropwise at 0° C. The mixture is subsequently stirred at 20° C. for 20 h. Precipitated triethylamine hydrochloride is filtered off with suction and washed with ethyl acetate. The combined mother liquors are washed twice with 50 ml of half-concentrated sodium chloride solution each time, dried over magnesium sulphate and concentrated under reduced pressure. 4.0 g (92.4% of theory) of crude 5-chloro-6-(4-chlorophenyl)-4-methoxycarbonyloxy-(2,4,6-trimethylphenyl)-2-pyrone are obtained. Recrystallization from 50 ml of cyclohexane affords 3.1 g (72% of theory) of pure product which melts at 136–138° C.

Similarly to Example (I-c-1) and/or according to the general preparation instructions, the compounds of the formula (I-c) listed in Table 3 below were obtained.

TABLE 3

(I-c)

$$\text{Structure: pyranone with } R^2\text{-O-C(O)-O- group, substituents A, D, and aryl group with X, Y, Z}_n$$

| Ex. No. | A | D | X | Y | $Z_n$ | $R^2$ | physical data m.p.; $^1$H-NMR (CDCl$_3$): δ [ppm] |
|---|---|---|---|---|---|---|---|
| I-c-2 | Cl | C(CH$_3$)$_3$ | CH$_3$ | CH$_3$ | 6-CH$_3$ | CH$_3$ | 6.97 (s, 2H); 3.76 (s, 3H); 2.35 (s, 3H); 2.20 (s, 6H); 1.58 (s, 9H) |
| I-c-3 | Cl | C(CH$_3$)$_3$ | CH$_3$ | CH$_3$ | 6-CH$_3$ | CH(CH$_3$)—C$_2$H$_5$ | 6.89 (s, 2H); 4.55 (sx, 1H); 2.28 (s, 3H); 2.21 (s, 6H); 1.50 (s, 6H); 1.45 (m, 2H); 1.10 (d, 3H); 0.72 (t, 3H) |
| I-c-4 | Cl | C$_6$H$_5$ | CH$_3$ | CH$_3$ | 6-CH$_3$ | CH$_3$ | 147–149° C. |
| I-c-5 | Cl | C$_6$H$_5$ | CH$_3$ | CH$_3$ | 6-CH$_3$ | CH(CH$_3$)—C$_2$H$_5$ | 74–76° C. |
| I-c-6 | Cl | 4-C$_6$H$_4$F | CH$_3$ | CH$_3$ | 6-CH$_3$ | CH$_3$ | 144–146° C. |
| I-c-7 | Cl | 4-C$_6$H$_4$Cl | CH$_3$ | CH$_3$ | 6-CH$_3$ | CH$_3$ | 136–138° C. |
| I-c-8 | Cl | 4-F-C$_6$H$_4$-CH$_2$- | C$_2$H$_5$ | Br | 6-C$_2$H$_5$ | C$_2$H$_5$ | 117–119° C. |
| I-c-9 | Cl | 4-F-C$_6$H$_4$-CH$_2$- | Cl | H | 6-CH$_3$ | C$_2$H$_5$ | 100–102° C. |
| I-c-10 | Cl | C(CH$_3$)$_3$ | Cl | H | 6-CH$_3$ | C$_2$H$_5$ | 4.13 (q, 2H); 2.23 (s, 3H); 1.53 (s, 9H); 1.13 (t, 3H) |

USE EXAMPLES

Example A

Phaedon Larvae Test

| Solvent: | 7 parts by weight of | acetone |
|---|---|---|
| Emulsifier: | 1 part by weight of | alkylaryl polyglycol ether |

To produce a suitable active compound preparation, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the active compound preparation of the desired concentration and populated with larvae of the mustard beetle (*Phaedon cochleariae*) while the leaves are still moist.

After the desired period of time, the plants are populated with larvae of the mustard beetle (Phaedon cochleariae). After in each case 3 days, the kill in % is determined. 100% means that all beetle larvae have been killed; 0% means that none of the beetle larvae have been killed.

In this test, for example the compounds of Preparation Examples I-a-1, I-a-2, I-a-4, I-b-1, I-b-2, I-b-7, I-b-8, I-c-1 and I-c-6 exhibited, at an exemplary active compound concentration of 0.01%, a kill of 100% after 7 days.

Example B

Plutella Test

| Solvent: | 7 parts by weight of | dimethyl formamide |
|---|---|---|
| Emulsifier: | 1 part by weight of | alkylaryl polyglycol ether |

To produce a suitable active compound preparation, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the active compound preparation of the desired concentration and populated with caterpillars of the diamond-back moth (*Plutella maculipennis*) while the leaves are still moist.

After the desired period of time, the kill in % is determined. 100% means that all caterpillars have been killed; 0% means that none of the caterpillars have been killed.

In this test, for example the compounds of Preparation Examples I-a-1, I-a-4, I-a-9, I-b-1, I-b-2, I-b-4, I-b-7, I-b-8, I-c-1, I-c-2 and I-c-6 exhibited, at an exemplary active compound concentration of 0.1%, a kill of 100% after 7 days.

Example C

Spodoptera Test

| Solvent:    | 7 parts by weight of | dimethyl formamide       |
|-------------|----------------------|--------------------------|
| Emulsifier: | 1 part by weight of  | alkylaryl polyglycol ether |

To produce a suitable active compound preparation, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the active compound preparation of the desired concentration and populated with caterpillars of the owlet moth (*Spodoptera frugiperda*) while the leaves are still moist.

After the desired period of time, the kill in % is determined. 100% means that all caterpillars have been killed; 0% means that none of the caterpillars have been killed.

In this test, for example the compounds of Preparation Examples I-b-1, I-c-2 and I-c-5 exhibited, at an exemplary active compound concentration of 0.1%, a kill of 85 to 100% after 7 days.

Example D

Nephotettix Test

| Solvent:    | 7 parts by weight of | dimethyl formamide       |
|-------------|----------------------|--------------------------|
| Emulsifier: | 1 part by weight of  | alkylaryl polyglycol ether |

To produce a suitable active compound preparation, 1 part by weight of active compound is mixed with the stated amount of solvent and the stated amount of emulsifier, and the concentrate is diluted with water to the desired concentration.

Rice seedlings (*Oryzae sativa*) are treated by being dipped into the active compound preparation of the desired concentration and populated with larvae of the green rice leaf hopper (*Nephotettix cincticeps*) while the seedlings are still moist.

After the desired period of time, the kill in % is determined. 100% means that all leaf hoppers have been killed; 0% means that none of the leaf hoppers have been killed.

In this test, for example the compounds of Preparation Examples I-a-3, I-a-4, I-a-9, I-a-10, I-a-11, I-b-2, I-b-7, I-c-2 and I-c-3 exhibited, at an exemplary active compound concentration of 0.1%, a kill of 100% after 6 days.

Example E

Myzus Test

| Solvent:    | 3 parts by weight of | dimethyl formamide       |
|-------------|----------------------|--------------------------|
| Emulsifier: | 1 part by weight of  | alkylaryl polyglycol ether |

To produce a suitable active compound preparation, 1 part by weight of active compound is mixed with the stated amount of solvent and the stated amount of emulsifier, and the concentrate is diluted with water to the desired concentration.

Cabbage leaves (*Brassica oleracea*) which are heavily infested by the green peach aphid (*Myzus persicae*) are treated by being dipped into the active compound preparation of the desired concentration.

After the desired period of time, the kill in % is determined. 100% means that all aphids have been killed; 0% means that none of the aphids have been killed.

In this test, for example the compounds of Preparation Examples I-a-1, I-a-4, I-a-5, I-a-9, I-a-11, I-b-4 and I-b-7 exhibited, at an exemplary active compound concentration of 0.1%, a kill of 80 to 100% after 6 days.

Example F

Tetranychus Test (resistant)

| Solvent:    | 3 parts by weight of | dimethyl formamide       |
|-------------|----------------------|--------------------------|
| Emulsifier: | 1 part by weight of  | alkylaryl polyglycol ether |

To produce a suitable active compound preparation, 1 part by weight of active compound is mixed with the stated amount of solvent and the stated amount of emulsifier, and the concentrate is diluted with water to the desired concentration.

Bean plants (*Phaseolus vulgaris*) which are heavily infested by all development stages of the greenhouse red spider mite (*Tetranychus urticae*) are treated by being dipped into the active compound preparation of the desired concentration.

After the desired period of time, the kill in % is determined. 100% means that all spider mites have been killed; 0% means that none of the spider mites have been killed.

In this test, for example the compounds of Preparation Examples I-a-3, I-a-4, I-a-11, I-b-1, I-c-2 and I-c-3 exhibited, at an exemplary active compound concentration of 0.01%, a kill of at least 95% after 13 days.

Example G

Pre-emergence Test

| Solvent:    | 5 parts by weight of | acetone                  |
|-------------|----------------------|--------------------------|
| Emulsifier: | 1 part by weight of  | alkylaryl polyglycol ether |

To produce a suitable active compound preparation, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the active compound preparation. For this purpose, the amount of water per unit area is advantageously kept constant. The active compound concentration in the preparation is not important, only the active compound application rate per unit area matters. After three weeks, the degree of damage to the plants is scored visually in % damage by comparison with the development of the untreated control. The figures denote:

0% = no activity (like untreated control)

100% = total destruction

In this test, for example the following compounds of the Preparation Examples exhibited very strong activity against weeds while some of them had very good crop plant safety.:

| Ex. No. | g/ha | Hordeum vulgare | Glycine max | Alopecurus myo- suroides | Echino- chloa crusgali | Lolium perenne | Abutilon theo- phrasti | Matri- caria inodora |
|---|---|---|---|---|---|---|---|---|
| I-a-3 | 500 | 0 | 0 | — | 95 | 100 | 100 | 60 |
| I-a-4 | 1000 | 0 | 0 | 90 | 100 | 95 | — | 90 |

Example H
Test With Flies (Musca domestica)
Test animals: adult Musca domestica, Reichswald strain (OP, SP carbamate-resistant)

| Solvent: | 35 parts by weight of ethylene glycol monomethyl ether |
| | 35 parts by weight of nonylphenol polyglycol ether |

To produce a suitable formulation, 3 parts by weight of active compound are mixed with 7 parts of the abovementioned solvent-emulsifier mixture, and the resulting emulsion concentrate is diluted with water to the respective desired concentration.

2 ml of this active compound preparation are pipetted onto filter paper dishes (φ 9.5 cm) situated in Petri dishes of corresponding size. After the filter discs have dried, 25 test animals are transferred into the Petri dishes and covered.

The activity of the active compound preparation is determined after 1, 3, 5 and 24 hours. 100% means that all the flies have been killed; 0% means that none of the flies have been killed.

In this test, for example the compound of Preparation Example I-c-4 had an activity of 100% at an exemplary active compound concentration of 1000 ppm.

Example I
Test with Fly Larvae/Development-inhibitory Action
Test animals: All larval stages of Lucilia cuprina (OP resistant)
[Pupae and adults (without contact with the active compound)]

| Solvent: | 35 parts by weight of ethylene glycol monomethyl ether |
| | 35 parts by weight of nonylphenol polyglycol ether |

To produce a suitable formulation, 3 parts by weight of active compound are mixed with 7 parts of the abovementioned solvent-emulsifier mixture, and the resulting emulsion concentrate is diluted with water to the respective desired concentration.

For each individual concentration, 30 to 50 larvae are introduced into a test tube which contains 1 cm³ of horsemeat. 500 μl of the dilution to be tested are pipetted onto this horsemeat. The test tubes are placed in plastic beakers whose bottom is covered with sea sand, and kept in an air-conditioned room (26° C.±1.5° C., 70%±10% relative humidity). The activity is examined (larvicidal action) after 24 hours and again after 48 hours. After emergence of the larvae (about 72 h), the test tubes are removed and perforated plastic lids are fitted onto the beakers. After 1.5 times the development time (hatching of the control flies), the hatched flies and the pupae/cocoons are counted.

The activity criterion is the incidence of death in the treated larvae after 48 h (larvicidal effect), or the inhibition of the hatching of adults from the pupae or the inhibition of pupae formation. The criterion for the in vitro activity of a substance is the inhibition of the development of the fleas, or a development standstill before the adult stage. 100% larvicidal action means that all the larvae have been killed after 48 hours. 100% development-inhibitory action means that no adult flies have hatched.

In this test, for example the compounds of Preparation Examples I-a-2, I-a-3, I-c-4, I-b-2 and I-c-5 exhibited, at an exemplary active compound concentration of 1000 ppm, an activity of 100%.

Example J
Test with Boophilus Microplus Resistant/SP-resistant Parkhurst Strain
Test animals: Adult females which have sucked themselves full
Solvent: Dimethyl sulphoxide 20 mg of active compound are dissolved in 1 ml of dimethyl sulphoxide, and weaker concentrations are prepared by dilution with the same solvent.

The test is carried out in 5 replications. 1 μl of the solutions is injected into the abdomen, and the animals are transferred into dishes and kept in a controlled-environment room. The activity is determined via the inhibition of oviposition. 100% means that no tick has deposited eggs.

In this test, for example the compound of Example I-a-9 exhibited, at an exemplary active compound concentration of 20 μg/animal, an activity of 100%.

We claim:
1. Compounds of the formula (I)

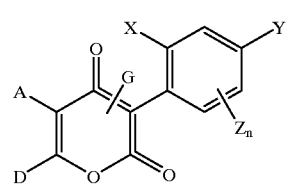

in which
X represents halogen, nitro, cyano, alkyl, alkenyl, alkoxy, alkenyloxy, alkylthio, alkylsulphinyl, alkylsulphonyl, halogenoalkyl, halogenoalkenyl, halogenoalkoxy, halogenoalkenyloxy or respectively optionally substituted phenyl, phenoxy, phenylthio, benzyloxy or benzylthio,
Y represents hydrogen, halogen, nitro, cyano, alkyl, alkenyl, alkoxy, alkenyloxy, alkylthio, alkylsulphinyl, alkylsulphonyl, halogenoalkyl, halogenoalkenyl, halogenoalkoxy or halogenoalkenyloxy,
Z represents halogen, nitro, cyano, alkyl, alkenyl, alkoxy, alkenyloxy, halogenoalkyl, halogenoalkenyl, halogenoalkoxy or halogenoalkenyloxy, n represents one of the numbers 0, 1, 2 or 3, A represents halogen, D represents hydrogen or represents an optionally substituted radical from the group consisting of alkyl, alkenyl, alkinyl, alkoxyalkyl, polyalkoxyalkyl, alkylthioalkyl saturated or unsaturated cycloalkyl, saturated or unsaturated heterocyclyl, arylalkyl, aryl, hetarylalkyl and hetaryl and G represents hydrogen (a) or represents one of the groups (b)
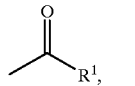

(c)
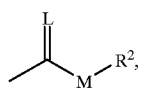

(d)
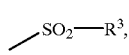

(e)
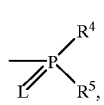

(f)
E
or (g)
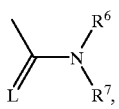

in which

E represents a metal ion equivalent or an ammonium ion,

L represents oxygen or sulphur,

M represents oxygen or sulphur, $R^1$ represents respectively optionally halogen-substituted alkyl, alkenyl, alkoxyalkyl, alkylthioalkyl or polyalkoxyalkyl or represents respectively optionally halogen-, alkyl- or alkoxy-substituted cycloalkyl or heterocyclyl or represents respectively optionally substituted phenyl, phenylalkyl, hetaryl, phenoxyalkyl or hetaryloxyalkyl, $R^2$ represents respectively optionally halogen-substituted alkyl, alkenyl, alkoxyalkyl or polyalkoxyalkyl or represents respectively optionally substituted cycloalkyl, phenyl or benzyl, $R^3$, $R^4$ and $R^5$ independently of one another each represent respectively optionally halogen-substituted alkyl, alkoxy, alkylamino, dialkylamino, alkylthio, alkenylthio or cycloalkylthio or represent respectively optionally substituted phenyl, benzyl, phenoxy or phenylthio, $R^6$ and $R^7$ independently of one another each represent hydrogen, represent respectively optionally halogen-substituted alkyl, cycloalkyl, alkenyl, alkoxy, alkoxyalkyl, represent respectively optionally substituted phenyl or benzyl, or, together with the linking nitrogen atom, form an optionally oxygen- or sulphur-containing cycle with the proviso that Z may not represent alkyl if X represents methyl, Y represents methyl and G represents hydrogen.

2. Compounds of the formula (I) according to claim 1, in which

X represents fluorine, chlorine, bromine, iodine, nitro, cyano, $C_1$–$C_8$-alkyl, $C_2$–$C_6$-alkenyl, $C_1$–$C_6$-alkoxy, $C_2$–$C_6$-alkenyloxy, $C_1$–$C_6$-alkylthio, $C_1$–$C_6$-alkylsulphinyl, $C_1$–$C_6$-alkylsulphonyl, represents respectively fluorine-, chlorine- or bromine-substituted $C_1$–$C_6$-alkyl, $C_2$–$C_6$-alkenyl, $C_1$–$C_6$-alkoxy or $C_2$–$C_6$-alkenyloxy or represents phenyl, phenoxy, phenylthio, benzyloxy or benzylthio, each of which is optionally substituted by fluorine, chlorine, bromine, iodine, nitro, cyano, or by respectively optionally fluorine-, chlorine- or bromine-substituted $C_1$–$C_6$-alkyl or $C_1$–$C_6$-alkoxy, Y represents hydrogen, fluorine, chlorine, bromine, iodine, nitro, cyano, $C_1$–$C_8$-alkyl, $C_2$–$C_6$-alkenyl, $C_1$–$C_6$-alkoxy, $C_2$–$C_6$-alkenyloxy, $C_1$–$C_6$-alkylthio, $C_1$–$C_6$-alkylsulphinyl, $C_1$–$C_6$-alkylsulphonyl or represents respectively fluorine-, chlorine- or bromine-substituted $C_1$–$C_6$-alkyl, $C_2$–$C_6$-alkenyl, $C_1$–$C_6$-alkoxy or $C_2$–$C_6$-alkenyloxy, Z represents fluorine, chlorine, bromine, iodine, nitro, cyano, $C_1$–$C_8$-alkyl, $C_2$–$C_6$-alkenyl, $C_1$–$C_6$-alkoxy, $C_2$–$C_6$-alkenyloxy or respectively fluorine-, chlorine- or bromine-substituted $C_1$–$C_6$-alkyl, $C_2$–$C_6$-alkenyl, $C_1$–$C_6$-alkoxy or $C_2$–$C_6$-alkenyloxy, n represents one of the numbers 0, 1, 2 or 3, A represents fluorine, chlorine, bromine or iodine, D represents hydrogen, represents respectively optionally halogen-substituted $C_1$–$C_{12}$-alkyl, $C_3$–$C_8$-alkenyl, $C_3$–$C_8$-alkinyl, $C_1$–$C_{10}$-alkoxy-$C_2$–$C_8$-alkyl, poly-$C_1$–$C_8$-alkoxy-$C_2$–$C_8$-alkyl or $C_1$–$C_{10}$-alkylthio-$C_2$–$C_8$-alkyl, represents cyano-, $C_1$–$C_8$-alkyloxycarbonyl- or $C_1$–$C_8$-alkylcarbonyloxy-substituted $C_1$–$C_{12}$-alkyl, represents optionally halogen-, $C_1$–$C_4$-alkyl, $C_1$–$C_4$-alkoxy- or $C_1$–$C_4$-halogenoalkyl-substituted $C_3$–$C_8$-cycloalkyl in which optionally one or two not directly adjacent methylene groups are replaced by oxygen and/or sulphur or represents respectively optionally halogen-, $C_1$–$C_6$-alkyl-, $C_1$–$C_6$-halogenoalkyl-, $C_1$–$C_6$-alkoxy-, $C_1$–$C_6$-halogenoalkoxy-, cyano- or nitro-substituted phenyl, hetaryl having 5 to 6 ring atoms and one or two hetero atoms from the group consisting of oxygen, sulphur and nitrogen, phenyl-$C_1$–$C_6$-alkyl or hetaryl-$C_1$–$C_6$-alkyl having 5 to 6 ring atoms and one or two hetero atoms from the group consisting of oxygen, sulphur and nitrogen, G represents hydrogen (a) or represents one of the groups (b)
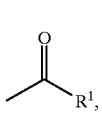

(c)
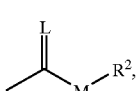

(d)
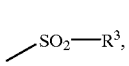

-continued

(e)

E
or
(f)

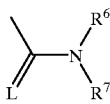
(g)

in which
E represents a metal ion equivalent or an ammonium ion,
L represents oxygen or sulphur and
M represents oxygen or sulphur,
$R^1$ represents respectively optionally halogen-substituted $C_1$–$C_{20}$-alkyl, $C_2$–$C_{20}$-alkenyl, $C_1$–$C_8$-alkoxy-$C_1$–$C_8$-alkyl, $C_1$–$C_8$-alkylthio-$C_1$–$C_8$-alkyl or poly-$C_1$–$C_8$-alkoxy-$C_1$–$C_8$alkyl or represents optionally halogen-, $C_1$–$C_6$-alkyl- or $C_1$–$C_6$-alkoxy-substituted $C_3$–$C_8$-cycloalkyl in which optionally one or two not directly adjacent methylene groups are replaced by oxygen and/or sulphur,
represents optionally halogen-, cyano-, nitro-, $C_1$–$C_6$-alkyl-, $C_1$–$C_6$-alkoxy-, $C_1$–$C_6$-halogenoalkyl-, $C_1$–$C_6$-halogenoalkoxy-, $C_1$–$C_6$-alkylthio- or $C_1$–$C_6$-alkylsulphonyl-substituted phenyl,
represents optionally halogen-, nitro-, cyano-, $C_1$–$C_6$-alkyl-, $C_1$–$C_6$-alkoxy-, $C_1$–$C_6$-halogenoalkyl- or $C_1$–$C_6$-halogenoalkoxy-substituted phenyl-$C_1$–$C_6$-alkyl,
represents optionally halogen- or $C_1$–$C_6$-alkyl-substituted 5- or 6-membered hetaryl having one or two hetero atoms from the group consisting of oxygen, sulphur and nitrogen,
represents optionally halogen- or $C_1$–$C_6$-alkyl-substituted phenoxy-$C_1$–$C_6$-alkyl or
represents optionally halogen-, amino- or $C_1$–$C_6$-alkyl-substituted 5- or 6-membered hetaryloxy-$C_1$–$C_6$-alkyl having one or two hetero atoms from the group consisting of oxygen, sulphur and nitrogen,
$R^2$ represents respectively optionally halogen-substituted $C_1$–$C_{20}$-alkyl, $C_2$–$C_{20}$-alkenyl, $C_1$–$C_8$-alkoxy-$C_1$–$C_8$-alkyl- or poly-$C_1$–$C_8$-alkoxy-$C_2$–$C_8$-alkyl,
represents optionally halogen-, $C_1$–$C_6$-alkyl- or $C_1$–$C_6$-alkoxy-substituted $C_3$–$C_8$-cycloalkyl or
represents respectively optionally halogen-, cyano-, nitro-, $C_1$–$C_6$-alkyl-, $C_1$–$C_6$-alkoxy-, $C_1$–$C_6$-halogenoalkyl- or $C_1$–$C_6$-halogenoalkoxy-substituted phenyl or benzyl,
$R^3$ represents optionally halogen-substituted $C_1$–$C_8$-alkyl or represents respectively optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, cyano- or nitro-substituted phenyl or benzyl,
$R^4$ and $R^5$ independently of one another each represent respectively optionally halogen-substituted $C_1$–$C_8$-alkyl, $C_1$–$C_8$-alkoxy, $C_1$–$C_8$-alkylamino, di-($C_1$–$C_8$-alkyl)amino, $C_1$–$C_8$-alkylthio or $C_2$–$C_8$-alkenylthio or represent respectively optionally halogen-, nitro-, cyano-, $C_1$–$C_4$-alkoxy-, $C_1$–$C_4$-halogenoalkoxy-, $C_1$–$C_4$-alkylthio-, $C_1$–$C_4$-halogenoalkylthio-, $C_1$–$C_4$-alkyl- or $C_1$–$C_4$-halogenoalkyl-substituted phenyl, phenoxy or phenylthio and
$R^6$ and $R^7$ independently of one another each represent hydrogen, represent respectively optionally halogen-substituted $C_1$–$C_8$-alkyl, $C_3$–$C_8$-cycloalkyl, $C_1$–$C_8$-alkoxy, $C_3$–$C_8$-alkenyl or $C_1$–$C_8$-alkoxy-$C_2$–$C_8$-alkyl, represent respectively optionally halogen-, $C_1$–$C_8$-alkyl-, $C_1$–$C_8$-halogenoalkyl- or $C_1$–$C_8$-alkoxy-substituted phenyl or benzyl or together represent a $C_3$–$C_6$-alkylene radical in which optionally one methylene group is replaced by oxygen or sulphur with the proviso that Z may not represent alkyl if X represents methyl, Y represents methyl and G represents hydrogen.

3. Compounds of the formula (I) accoarding to claim 1, in which

X represents fluorine, chlorine, bromine, nitro, cyano, $C_1$–$C_6$-alkyl, $C_2$–$C_4$-alkenyl, $C_1$–$C_4$-alkoxy, $C_2$–$C_4$-alkenyloxy, $C_1$–$C_4$-alkylthio, $C_1$–$C_4$-alkylsulphinyl, $C_1$–$C_4$-alkylsulphonyl, represents respectively fluorine- or chlorine-substituted $C_1$–$C_4$-alkyl, $C_2$–$C_4$-alkenyl, $C_1$–$C_4$-alkoxy or $C_1$–$C_4$-alkenyloxy or represents phenyl, phenoxy, phenylthio, benzyloxy or benzylthio, each of which is optionally substituted by fluorine, chlorine, bromine, nitro, cyano or by respectively optionally fluorine- or chlorine-substituted $C_1$–$C_4$-alkyl or $C_1$–$C_4$-alkoxy, Y represents hydrogen, fluorine, chlorine, bromine, nitro, cyano, $C_1$–$C_6$-alkyl, $C_2$–$C_4$-alkenyl, $C_1$–$C_4$-alkoxy, $C_2$–$C_4$-alkenyloxy, $C_1$–$C_4$-alkylthio, $C_1$–$C_4$-alkylsulphinyl, $C_1$–$C_4$-alkylsulphonyl or represents respectively fluorine- or chlorine-substituted $C_1$–$C_4$-alkyl or $C_1$–$C_4$-alkoxy, Z represents fluorine, chlorine, bromine, nitro, cyano, $C_1$–$C_6$-alkyl, $C_1$–$C_4$-alkoxy, $C_2$–$C_4$-alkenyloxy or respectively fluorine- or chlorine-substituted $C_1$–$C_4$-alkyl or $C_1$–$C_4$-alkoxy, n represents one of the numbers 0, 1 or 2, A represents fluorine, chlorine or bromine, D represents hydrogen, represents respectively optionally fluorine- or chlorine-substituted $C_1$–$C_{10}$-alkyl, $C_3$–$C_6$-alkenyl, $C_3$–$C_6$-alkinyl, $C_1$–$C_8$-alkoxy-$C_2$–$C_6$-alkyl, poly-$C_1$–$C_6$-alkoxy-$C_2$–$C_6$-alkyl or $C_1$–$C_8$-alkylthio-$C_2$–$C_6$-alkyl, represents cyano-, $C_1$–$C_6$-alkoxycarbonyl- or $C_1$–$C_6$-alkylcarbonyloxy-substituted $C_1$–$C_8$-alkyl, represents optionally fluorine-, chlorine-, $C_1$–$C_4$-alkyl-, $C_1$–$C_4$-alkoxy- or $C_1$–$C_2$-halogenoalkyl-substituted $C_3$–$C_7$-cycloalkyl in which optionally one or two not directly adjacent methylene groups are replaced by oxygen and/or sulphur or represents respectively optionally fluorine-, chlorine-, bromine-, $C_1$–$C_4$-alkyl-, $C_1$–$C_4$-halogenoalkyl-, $C_1$–$C_4$-alkoxy-, $C_1$–$C_4$-halogenoalkoxy-, cyano- or nitro-substituted phenyl, furanyl, imidazolyl, pyridyl, thiazolyl, pyrazolyl, pyrimidyl, pyridazyl, pyrazinyl, pyrrolyl, thienyl, triazolyl or phenyl-$C_1$–$C_4$-alkyl, G represents hydrogen (a) or represents one of the groups

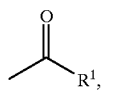
(b)

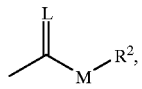
(c)

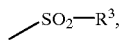
(d)

(e)

E   (f)
or

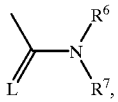
(g)

in which
E represents a metal ion equivalent or an ammonium ion,
L represents oxygen or sulphur and
M represents oxygen or sulphur,
$R^1$ represents respectively optionally fluorine- or chlorine-substituted $C_1$–$C_{16}$-alkyl, $C_2$–$C_{16}$-alkenyl, $C_1$–$C_6$-alkoxy-$C_1$–$C_6$-alkyl, $C_1$–$C_6$-alkylthio-$C_1$–$C_6$-alkyl or poly-$C_1$–$C_6$-alkoxy-$C_1$–$C_6$-alkyl or represents optionally fluorine-, chlorine-, $C_1$–$C_5$-alkyl- or $C_1$–$C_5$-alkoxy-substituted $C_3$–$C_7$-cycloalkyl in which optionally one or two not directly adjacent methylene groups are replaced by oxygen and/or sulphur,
represents optionally fluorine-, chlorine-, bromine-, cyano-, nitro-, $C_1$–$C_4$-alkyl-, $C_1$–$C_4$-alkoxy-, $C_1$–$C_3$-halogenoalkyl-, $C_1$–$C_3$-halogeno-alkoxy-, $C_1$–$C_4$-alkylthio- or $C_1$–$C_4$-alkylsulphonyl-substituted phenyl,
represents optionally fluorine-, chlorine-, bromine-, $C_1$–$C_4$-alkyl-, $C_1$–$C_4$-alkoxy-, $C_1$–$C_3$-halogenoalkyl- or $C_1$–$C_3$-halogenoalkoxy-substituted phenyl-$C_1$–$C_4$-alkyl,
represents respectively optionally fluorine-, chlorine-, bromine- or $C_1$–$C_4$-alkyl-substituted pyrazolyl, thiazolyl, pyridyl, pyrimidyl, furanyl or thienyl,
represents optionally fluorine-, chlorine-, bromine- or $C_1$–$C_4$-alkyl-substituted phenoxy-$C_1$–$C_5$-alkyl or
represents respectively optionally fluorine-, chlorine-, bromine-, amino- or $C_1$–$C_4$-alkyl-substituted pyridyloxy-$C_1$–$C_5$-alkyl, pyrimidyloxy-$C_1$–$C_5$-alkyl or thiazolyloxy-$C_1$–$C_5$-alkyl,
$R^2$ represents respectively optionally fluorine- or chlorine-substituted $C_1$–$C_{16}$-alkyl, $C_2$–$C_{16}$-alkenyl, $C_1$–$C_6$-alkoxy-$C_2$–$C_6$-alkyl or poly-$C_1$–$C_6$-alkoxy-$C_2$–$C_6$-alkyl, represents optionally fluorine-, chlorine-, $C_1$–$C_4$-alkyl- or $C_1$–$C_4$-alkoxy-substituted $C_3$–$C_7$-cycloalkyl or
represents respectively optionally fluorine-, chlorine-, bromine-, cyano-, nitro-, $C_1$–$C_4$-alkyl-, $C_1$–$C_3$-alkoxy, $C_1$–$C_3$-halogenoalkyl or $C_1$–$C_3$-halogenoalkoxy-substituted phenyl or benzyl,
$R^3$ represents optionally fluorine- or chlorine-substituted $C_1$–$C_6$-alkyl or represents respectively optionally fluorine-, chlorine-, bromine-, $C_1$–$C_5$-alkyl-, $C_1$–$C_5$-alkoxy-, $C_1$–$C_3$-halogenoalkyl-, $C_1$–$C_3$-halogenoalkoxy-, cyano- or nitro-substituted phenyl or benzyl,
$R^4$ and $R^5$ independently of one another each represent respectively optionally fluorine- or chlorine-substituted $C_1$–$C_6$-alkyl, $C_1$–$C_6$-alkoxy, $C_1$–$C_6$-alkylamino, di-($C_1$–$C_6$-alkyl)amino, $C_1$–$C_6$-alkylthio or $C_3$–$C_4$-alkenylthio or represent respectively optionally fluorine-, chlorine-, bromine-, nitro-, cyano-, $C_1$–$C_3$-alkoxy-, $C_1$–$C_3$-halogeno-alkoxy-, $C_1$–$C_3$-alkylthio-, $C_1$–$C_3$-halogenoalkylthio-, $C_1$–$C_3$-alkyl- or $C_1$–$C_3$-halogenoalkyl-substituted phenyl, phenoxy or phenylthio and
$R^6$ and $R^7$ independently of one another each represent hydrogen, represent respectively optionally fluorine- or chlorine-substituted $C_1$–$C_6$-alkyl, $C_3$–$C_6$-cycloalkyl, $C_1$–$C_6$-alkoxy, $C_3$–$C_6$-alkenyl or $C_1$–$C_6$-alkoxy-$C_2$–$C_6$-alkyl, represent respectively optionally fluorine-, chlorine-, bromine-, $C_1$–$C_5$-halogenoalkyl-, $C_1$–$C_5$-alkyl- or $C_1$–$C_5$-alkoxy-substituted phenyl or benzyl, or together represent a $C_3$–$C_6$-alkylene radical in which optionally one methylene group is replaced by oxygen or sulphur
with the proviso that Z may not represent alkyl if X represents methyl, Y represents methyl and G represents hydrogen.
4. Compounds of the formula (I) according to claim 1, in which
X represents fluorine, chlorine, bromine, nitro, cyano, methyl, ethyl, n- or i-propyl, n-, s-, i- or t-butyl, vinyl, allyl, methallyl, methoxy, ethoxy, n- or i-propoxy, allyloxy, methallyloxy, trifluoromethyl, difluoromethoxy, trifluoromethoxy, trifluoroethoxy, methylthio, methylsulphinyl or methylsulphonyl,
Y represents hydrogen, fluorine, chlorine, bromine, nitro, cyano, methyl, ethyl, n- or i-propyl, n-, s-, i- or t-butyl, methoxy, ethoxy, n- or i-propoxy, allyloxy, methallyloxy, trifluoromethyl, difluoromethoxy, trifluoromethoxy, trifluoroethoxy, methylthio, methylsulphinyl or methylsulphonyl,
Z represents fluorine, chlorine, bromine, nitro, cyano, methyl, ethyl, n- or i-propyl, n-, s-, i- or t-butyl, methoxy, ethoxy, n- or i-propoxy, allyloxy, methallyloxy, trifluoromethyl, difluoromethoxy, trifluoromethoxy or trifluoroethoxy,
n represents one of the numbers 0 or 1,
A represents fluorine, chlorine or bromine,
D represents hydrogen, represents respectively optionally fluorine- or chlorine-substituted $C_1$–$C_8$-alkyl, $C_3$–$C_4$-alkenyl, $C_3$–$C_4$-alkinyl, $C_1$–$C_6$-alkoxy-$C_2$–$C_4$-alkyl, poly-$C_1$–$C_4$-alkoxy-$C_2$–$C_4$-alkyl, $C_1$–$C_4$-alkylthio-$C_2$–$C_4$-alkyl or $C_3$–$C_6$-cycloalkyl in which optionally one or two not directly adjacent methylene groups are replaced by oxygen and/or sulphur or represents respectively optionally fluorine-, chlorine-, bromine-, methyl-, ethyl-, n-propyl-, isopropyl-, methoxy-, ethoxy-, trifluoromethyl-, trifluoromethoxy-, cyano- or nitro-substituted phenyl, furanyl, pyridyl, thienyl or benzyl, G represents hydrogen (a) or represents one of the groups

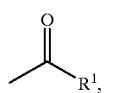
(b)

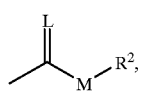
(c)

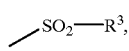
(d)

(e)

E
or
(f)

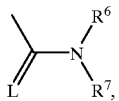
(g)

in which
E represents a metal ion equivalent or an ammonium ion,
L represents oxygen or sulphur and
M represents oxygen or sulphur,
$R^1$ represents respectively optionally fluorine- or chlorine-substituted $C_1$–$C_{14}$-alkyl, $C_2$–$C_{14}$-alkenyl, $C_1$–$C_4$-alkoxy-$C_1$–$C_6$-alkyl, $C_1$–$C_4$-alkylthio-$C_1$–$C_6$-alkyl, poly-$C_1$–$C_4$-alkoxy-$C_1$–$C_4$-alkyl or represents optionally fluorine-, chlorine-, methyl-, ethyl-, n-propyl-, i-propyl-, n-butyl-, i-butyl-, tert-butyl-, methoxy-, ethoxy-, n-propoxy- or isopropoxy-substituted $C_3$–$C_6$-cycloalkyl in which optionally one or two not directly adjacent methylene groups are replaced by oxygen and/or sulphur,
represents optionally fluorine-, chlorine-, bromine-, cyano-, nitro-, methyl-, ethyl-, n-propyl-, i-propyl-, methoxy-, ethoxy-, trifluoromethyl-, trifluoromethoxy-, methylthio-, ethylthio-, methyl sulphonyl- or ethylsulphonyl-substituted phenyl,
represents optionally fluorine-, chlorine-, bromine-, methyl-, ethyl-, n-propyl-, i-propyl-, methoxy-, ethoxy-, trifluoromethyl- or trifluoromethoxy-substituted benzyl,
represents respectively optionally fluorine-, chlorine-, bromine-, methyl- or ethyl-substituted furanyl, thienyl or pyridyl,
represents optionally fluorine-, chlorine-, methyl- or ethyl-substituted phenoxy-$C_1$–$C_4$-alkyl or
represents respectively optionally fluorine-, chlorine-, amino-, methyl- or ethyl-substituted pyridyloxy-$C_1$–$C_4$-alkyl, pyrimidyloxy-$C_1$–$C_4$-alkyl or thiazolyloxy-$C_1$–$C_4$-alkyl,
$R^2$ represents respectively optionally fluorine- or chlorine-substituted $C_1$–$C_{14}$-alkyl, $C_2$–$C_{14}$-alkenyl, $C_1$–$C_4$-alkoxy-$C_2$–$C_6$-alkyl or poly-$C_1$–$C_4$-alkoxy-$C_2$–$C_6$-alkyl,
represents optionally fluorine-, chlorine-, methyl-, ethyl-, n-propyl-, isopropyl- or methoxy-substituted $C_3$–$C_6$-cycloalkyl,
or represents respectively optionally fluorine-, chlorine-, cyano-, nitro-, methyl-, ethyl-, n-propyl-, i-propyl-, methoxy-, ethoxy-, trifluoromethyl- or trifluoromethoxy-substituted phenyl or benzyl,
$R^3$ represents optionally fluorine- or chlorine-substituted methyl, ethyl, propyl, isopropyl or respectively optionally fluorine-, chlorine-, bromine-, methyl-, ethyl-, propyl-, isopropyl-, tert-butyl-, methoxy-, ethoxy-, isopropoxy-, tert-butoxy-, trifluoromethyl-, trifluoromethoxy-, cyano- or nitro-substituted phenyl or benzyl,
$R^4$ and $R^5$ independently of one another each represent respectively optionally fluorine- or chlorine-substituted $C_1$–$C_4$-alkyl, $C_1$–$C_4$-alkoxy, $C_1$–$C_4$-alkylamino, di-($C_1$–$C_4$-alkyl)amino or $C_1$–$C_4$-alkylthio or represent respectively optionally fluorine-, chlorine-, bromine-, nitro-, cyano-, methyl-, methoxy-, trifluoromethyl- or trifluoromethoxy-substituted phenyl, phenoxy or phenylthio and
$R^6$ and $R^7$ independently of one another each represent hydrogen, represent respectively optionally fluorine- or chlorine-substituted $C_1$–$C_4$-alkyl, $C_3$–$C_6$-cycloalkyl, $C_1$–$C_4$-alkoxy, $C_3$–$C_4$-alkenyl or $C_1$–$C_4$-alkoxy-$C_2$–$C_4$-alkyl, represent respectively optionally fluorine-, chlorine-, bromine-, methyl-, methoxy- or trifluoromethyl-substituted phenyl or benzyl, or together represent a $C_5$–$C_6$-alkylene radical in which optionally one methylene group is replaced by oxygen or sulphur
with the proviso that Z may not represent alkyl if X represents methyl, Y represents methyl and G represents hydrogen.

5. Process for preparing compounds of the formula (I) according to claim 1, characterized in that
(A) Compounds of the formula (I-a)

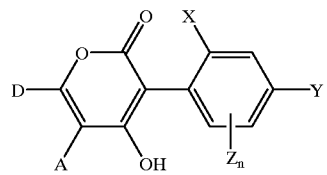
(I-a)

in which
A, D, X, Y, Z and n are each as defined in claim 1, are obtained when
compounds of the formula (II)

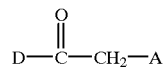
(II)

in which
A and D are each as defined above
are reacted with compounds of the formula (III)

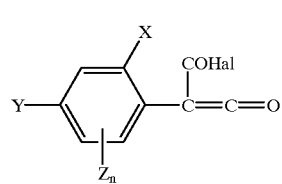
(III)

in which

X, Y, Z and n are each as defined above and
Hal represents halogen,
optionally in the presence of a diluent and optionally in the presence of an acid acceptor,
and, optionally the compounds of the formula (Ia) obtained in this manner are subsequently reacted (B) α) with acyl halides of the formula (IV)

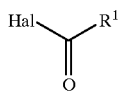 (IV)

in which
R¹ is as defined in claim 1 and
Hal represents halogen or

β) with carboxylic anhydrides of the formula (V)

$$R^1-CO-O-C-R^1 \quad (V)$$

in which
R¹ is as defined above,
optionally in the presence of a diluent and optionally in the presence of an acid binder or (C) with chloroformic acid esters or chloroformic acid thioesters of the formula (VI)

$$R^2-M-CO-Cl \quad (VI)$$

in which
R² and M are each as defined in claim 1,
optionally in the presence of a diluent and optionally in the presence of an acid binder, or (D) α) with chloromonothioformic acid esters or chlorodithioformic acid esters of the formula (VII)

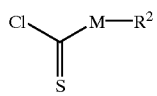 (VII)

in which
M and R² are each as defined in claim 1,
optionally in the presence of a diluent and optionally in the presence of an acid binder, or β) with carbon disulphide and subsequently with compounds of the formula (VIII)

$$R^2-Hal \quad (VIII)$$

in which
R² is as defined above and
Hal represents chlorine, bromine or iodine,
optionally in the presence of a diluent and optionally in the presence of base, or (E) with sulfonyl chlorides of the formula (IX)

$$R^3-SO_2-Cl \quad (IX)$$

in which
R³ is as defined in claim 1,
optionally in the presence of a diluent and optionally in the presence of an acid binder, or (F) with phosphorus compounds of the formula (X)

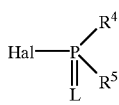 (X)

in which
L, R⁴ and R⁵ are each as defined in claim 1 and
Hal represents halogen,
optionally in the presence of a diluent and optionally in the presence of an acid binder, or (G) with metal compounds or amines of the formula (XI) or (XII)

$$(MeOR^9)_t \quad (XI)$$

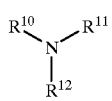 (XII)

in which
Me represents a mono- or bivalent metal,
t represents the number 1 or 2 and
R⁹, R¹⁰, R¹¹, R¹² independently of one another each represent hydrogen or alkyl (preferably C₁–C₈-alkyl),
optionally in the presence of a diluent, or (H) α) with isocyanates or isothiocyanates of the formula (XIII)

$$R^6-N=C=L \quad (XIII)$$

in which
R⁶ and L are each as defined in claim 1,
optionally in the presence of a diluent and optionally in the presence of a catalyst or β) with carbamyl chlorides or thiocarbamyl chlorides of the formula (XIV)

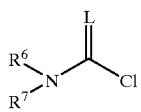 (XIV)

in which
L, R⁶ and R⁷ are each as defined above,
optionally in the presence of a diluent and optionally in the presence of an acid binder.

6. A pesticidal and herbicidal composition comprising at least one compound of the formula (I) according to claim 1 and an extender.

7. A method for controlling pests and weeds, which comprises applying an effective amount of a compound of the formula (I) according to claim 1 to such pests, weeds or their habitat.

* * * * *